(12) United States Patent
Nault et al.

(10) Patent No.: US 10,317,343 B2
(45) Date of Patent: *Jun. 11, 2019

(54) METHOD AND SYSTEM FOR SAMPLING AND ANALYZING ORGANIC MATERIAL

(71) Applicant: LOGIAG INC., Sainte-Martine (CA)

(72) Inventors: Charles Nault, Montreal (CA);
Christian Degrace, Magog (CA);
Gilles Clement, Eastman, CA (US);
Michel Corriveau,
St-Denis-de-Brompton (CA)

(73) Assignee: LOGIAG INC., Sainte-Martine (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/162,932

(22) Filed: Oct. 17, 2018

(65) Prior Publication Data

US 2019/0049387 A1 Feb. 14, 2019

Related U.S. Application Data

(63) Continuation of application No. 15/393,680, filed on Dec. 29, 2016, now Pat. No. 10,145,801, which is a
(Continued)

(51) Int. Cl.
*G01N 21/71* (2006.01)
*G01N 33/24* (2006.01)
(Continued)

(52) U.S. Cl.
CPC ............. *G01N 21/718* (2013.01); *G01N 1/04* (2013.01); *G01N 1/286* (2013.01); *G01N 1/44* (2013.01);
(Continued)

(58) Field of Classification Search
CPC ........ G01N 21/01; G01N 21/03; G01N 21/17; G01N 21/718; G01N 1/286; G01N 1/08;
(Continued)

(56) References Cited

U.S. PATENT DOCUMENTS 5,161,407 A 11/1992 Ankeny et al.
5,343,771 A 9/1994 Turriff et al.
(Continued)

FOREIGN PATENT DOCUMENTS

JP 2003172697 6/2003
WO 0201191 A2 1/2002

OTHER PUBLICATIONS

PCT Patent Application PCT/CA2015/050607 International Preliminary Report on Patentability dated Oct. 25, 2016.
(Continued)

*Primary Examiner* — Jamil Ahmed
(74) *Attorney, Agent, or Firm* — Erise IP, P.A.

(57) ABSTRACT

A system and a method are provided for sampling and analyzing organic material, including soil, fertilizer, manure and leaves. A sample container having porous sidewalls and a unique identifier is provided. A geographic position corresponding to a location where a sample was taken is associated with the unique identifier. The sample container with the sample contained therein is received, and the sample is compacted while inside the sample container. The sample is analyzed while inside the sample container using a Laser Induced Breakdown Spectroscopy (LIBS) system and analysis results are generated. The analysis results of the sample are associated with the unique identifier of the sample container.

36 Claims, 23 Drawing Sheets

Related U.S. Application Data continuation-in-part of application No. PCT/CA2015/050607, filed on Jun. 29, 2015.

(60) Provisional application No. 62/018,874, filed on Jun. 30, 2014.

(51) Int. Cl.
  G01N 1/28 (2006.01)
  G01N 1/04 (2006.01)
  G01N 1/44 (2006.01)
  G01N 1/02 (2006.01)
  G01N 1/00 (2006.01)
  G01N 35/00 (2006.01)

(52) U.S. Cl.
  CPC ....... *G01N 33/24* (2013.01); *G01N 35/00732* (2013.01); *G01N 2001/005* (2013.01); *G01N 2001/021* (2013.01)

(58) Field of Classification Search
  CPC .. G01N 1/04; G01N 1/28; G01N 1/44; G01N 33/24; G01N 35/00732; G01N 2001/005; G01N 2001/021; G01N 23/223; G01N 3/08; G06F 17/00; G01J 3/30; A23L 1/27; A23G 1/1118; B32B 3/00; B32B 17/10036; B44D 3/04; B44D 3/02; E02D 1/04

See application file for complete search history.

(56) References Cited

U.S. PATENT DOCUMENTS

| | | | |
|---|---|---|---|
| 5,470,535 A | 11/1995 | Ray et al. | |
| 5,505,098 A | 4/1996 | Turriff et al. | |
| 5,937,953 A | 8/1999 | Melberg et al. | |
| 6,016,713 A | 1/2000 | Hale | |
| 6,044,324 A | 3/2000 | Boerhave et al. | |
| 6,317,694 B1 | 11/2001 | Kram et al. | |
| 6,712,161 B1 | 3/2004 | Dai | |
| 6,772,651 B2 | 8/2004 | Scott et al. | |
| 7,105,220 B2 * | 9/2006 | Freeman | B32B 17/10036 428/172 |
| 7,172,036 B2 | 2/2007 | Jacobs et al. | |
| 7,216,725 B2 | 5/2007 | Jacobs et al. | |
| 7,275,682 B2 | 10/2007 | Excoffier et al. | |
| 7,552,654 B2 | 6/2009 | Burton | |
| 7,692,789 B1 | 4/2010 | Ebinger et al. | |
| 8,156,786 B2 | 4/2012 | Nowland | |
| 8,286,857 B2 | 10/2012 | Covely | |
| 8,685,339 B2 | 4/2014 | Forsythe et al. | |
| 8,897,973 B2 | 11/2014 | Hunt et al. | |
| 8,942,927 B2 | 1/2015 | Hermann | |
| 2002/0035431 A1 | 3/2002 | Ell | |
| 2005/0012244 A1 | 1/2005 | Jones | |
| 2005/0178211 A1 * | 8/2005 | Thom | G01N 3/08 73/820 |
| 2006/0000296 A1 | 1/2006 | Salter | |
| 2006/0286606 A1 | 12/2006 | Oliver | |
| 2007/0218556 A1 | 9/2007 | Harris et al. | |
| 2007/0269341 A1 | 11/2007 | Halverson et al. | |
| 2008/0107783 A1 * | 5/2008 | Anijs | A23G 1/0009 426/270 |
| 2008/0156667 A1 * | 7/2008 | Huggins | B44D 3/02 206/1.8 |
| 2009/0031790 A1 | 2/2009 | Guo et al. | |
| 2009/0270151 A1 * | 10/2009 | Moody | A63F 3/00157 463/13 |
| 2009/0290151 A1 | 11/2009 | Agrawal et al. | |
| 2010/0288059 A1 | 11/2010 | Viljoen et al. | |
| 2011/0240730 A1 * | 10/2011 | Covely | E02D 1/04 235/375 |
| 2016/0178434 A1 * | 6/2016 | Buckley | G01J 3/0248 356/72 |

OTHER PUBLICATIONS

PCT Patent Application PCT/CA2015/050607 International Search Report dated Aug. 20, 2015.
PCT Patent Application PCT/CA2015/050607 Written Opinion of the International Searching Authority dated Sep. 4, 2015.
Extended European Search Report dated Jan. 29, 2018; EP Application No. 15815475.7; Applicant: Logiag Inc.

* cited by examiner

6. Report: A report is generated using the analysis results and can be viewed by the client over the web.

7. Archiving: The samples are archived within the sample group box for a period of 6 months, according to ISO 17025 standards.

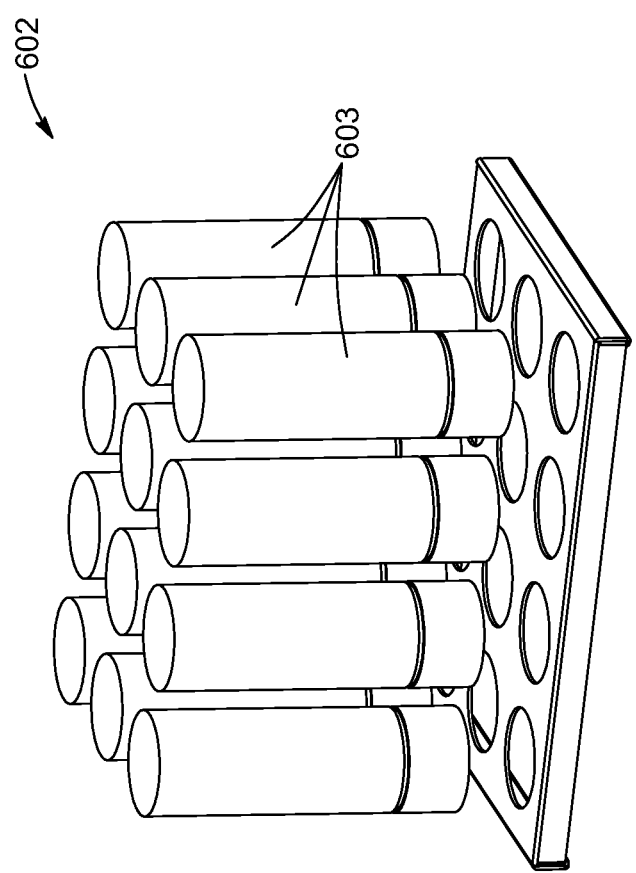

Analysis made by: John D.

Analysis submitted by: Soil Co

/ Sample name:

Sampler name: Chris P.
Sample date: April 17th, 2014
Sampling date: April 17th, 2014
Reception date: April 19th, 2014
Analysis date: April 21st, 2014
Report date: April 21st, 2014
Method: Laser-Induced Breakdown Spectroscopy (LIBS)
Preparation: Soil dried (37°C) and pressed (23t)

Analysis Results

| Nutriments (kg/ha) | |
|---|---|
| Phosphorus (P) | 309 |
| Potassium (K) | 338 |
| Calcium (Ca) | 6258 |
| Magnesium (Mg) | 495 |
| Aluminium (Al) (ppm) | 1175 |

| Trace elements (ppm) | |
|---|---|
| Manganese (Mn) | 15,70 |
| Copper (Cu) | 4,44 |
| Boron (B) | 16,27 |
| Zinc (Zn) | 0,55 |
| Sulfur (S) | - |

| Others | |
|---|---|
| pH (water) | 6,4 |
| Organic matter (%) | 3,92 |
| Zinc (Zn) | 19,4 |

FIG. 10

METHOD AND SYSTEM FOR SAMPLING AND ANALYZING ORGANIC MATERIAL

RELATED APPLICATIONS

The present application is a continuation patent application and claims priority benefit, with regard to all common subject matter, of U.S. patent application Ser. No. 15/393,680, filed Dec. 29, 2016 ("the '680 Application"), now U.S. Pat. No. 10,145,801. The '680 Application is a continuation-in-part application and claims priority benefit, with regard to all common subject matter, of PCT Patent Application No. PCT/CA2015/050607, filed Jun. 29, 2015, which claims priority to U.S. Provisional Patent Application No. 62/018,874, filed Jun. 30, 2014. The above-referenced applications are herein incorporated by reference in their entirety.

BACKGROUND OF THE INVENTION

In the agriculture industry, agronomists often have to establish and follow an agro-environmental fertilization plan when cultivating a field. Such a plan determines the spreading limits for fertilizers for a given growing season. In order to best determine the fertilization needs of a particular area of land, it is often necessary to analyze soil samples in order to measure pH, and the concentration of several minerals, such as potassium, phosphorus, magnesium, aluminum and calcium, among others.

Current methods for analyzing samples involve four main steps: (1) collecting a soil sample; (2) transporting the sample to a laboratory and preparing it for analysis; (3) dissolving the sample chemically; and (4) analyzing the sample using methods such as Inductively Coupled Plasma Atomic Emission Spectroscopy (ICP-OES) or Flame Atomic Absorption Spectrometry (FAAS).

These methods involve many different physical and chemical operations, both when preparing and analyzing samples. For example, many samples must be collected from several locations and prepared for transport to a lab. Next, the samples are subject to a laborious analyzing process involving drying, grinding, sieving, extracting and filtering.

Existing methods are both time consuming and expensive. For example, these methods require large individual samples (approximately 500 g) from various parts of a field which must each be transported to a lab. Once at the lab, analyzing the soil may require several different tests in order to analyze different characteristics of the soil. These tests can take a significant amount of time, making the turnaround time relatively slow.

In existing methods, there is also a significant risk that samples can become contaminated and/or confused. For example, identification information is often hand-written on sample containers, making identification difficult when the identification information contains mistakably similar characters, or when it is written with poor handwriting. What's more, in order to carry out a test, a portion of a soil sample must be transferred into a separate test container, creating an opportunity to introduce contaminants or lose track of a sample.

U.S. Pat. No. 8,286,857 describes a soil sample tracking system and method in which soil sample containers are provided with unique identifiers. The containers are used to temporarily store the soil samples until they are analyzed. The soil samples must thus be removed from their containers for analysis, and thus there is still a risk of mixing or contaminating the different soil samples.

These shortcomings have a significant impact on the use of such methods in practice. For example, due to the costs involved, many agronomists generally limit sampling to a single sample per field. This is not ideal, as it does not provide sufficiently fine-grained information about the soil characteristics of a field, and thus limits the effectiveness of an agro-environmental fertilization plan when it is based on that information.

Some improvements have already been made to the step of analyzing a sample in the laboratory. For example, soil can be analyzed using a method known as Laser Induced Breakdown Spectroscopy (LIBS), such as the method disclosed in U.S. Pat. No. 7,692,789. While this technology is an improvement in the lab, there is yet to be a practical method for using LIBS technology in the context of gathering several samples of soil from a field and managing data from the analysis of those samples.

There is therefore a need for an improved method and system which reduces costs and simplifies the overall process of sampling and analyzing soil by leveraging LIBS technology.

SUMMARY OF THE INVENTION

It is therefore an object of the present invention to provide a method and system for improving the sampling and analysis of organic material, including the sampling and analysis of soil in the context of the agriculture industry. Organic material, or organic matter, encompasses soil, fertilizer, manure, leaves or any other carbon-based compounds found in natural, engineered, terrestrial and aquatic environment.

According to an aspect, a method for sampling and analyzing organic material is provided. The method includes the steps of: providing a sample container having porous sidewalls and a unique identifier; associating, on a database, a geographic position with the unique identifier, the geographic position corresponding to a location where an organic material sample was taken; receiving the sample container with the organic material sample contained therein; compacting the organic material sample while inside the sample container; analyzing the organic material sample while inside the sample container using a Laser Induced Breakdown Spectroscopy (LIBS) system and generating analysis results; and associating the analysis results of the organic material sample with the unique identifier of the sample container.

In an embodiment, the organic material sample is dried while inside the sample container below a humidity level of approximately 10%.

In an embodiment, drying the organic material sample includes heating the organic material sample inside an oven at a temperature between approximately 30° C. and 45° C. for a period of between approximately 2 hours and 48 hours.

In an embodiment, compacting the organic material sample comprises hydraulically pressing the organic material sample with a weight of between approximately 15 tonnes and 30 tonnes.

In an embodiment, the organic material sample contained in the sample container is between approximately 5 grams and 150 grams.

In an embodiment, a plurality of organic material samples is analyzed sequentially in the LIBS system as part of a batch.

In an embodiment, analyzing the organic material sample is performed in less than 60 seconds.

In an embodiment, the batch includes at least one control sample for calibrating the LIBS system; between approximately 10% and 20% of the organic material samples in the batch can be control samples. In an alternate embodiment, the LIBS system can be pre-calibrated prior to analyzing the batch.

In an embodiment, the plurality of organic material samples is compacted sequentially as part of a batch.

In an embodiment, the method further includes a step of loading the plurality of organic material samples in a support tray, with at least one of the steps of drying, compacting, analyzing and archiving being performed while the soil samples are in the support tray.

In an embodiment, the unique identifier within the LIBS system is scanned prior to performing the analysis of the organic material sample.

In an embodiment, analyzing the organic material sample using the LIBS system includes shining a laser on a plurality of different areas on an exposed surface of the organic material sample.

In an embodiment, the method further includes the steps of receiving report preferences from a user and generating a report summarizing the analysis according to the report preferences.

In an embodiment, the method further includes the step of grouping a plurality of sample containers in a sample group box and mailing the sample group box via a postal service.

In an embodiment, the method further includes the step of providing the sample group box with a pre-paid postage label for returning the sample group box to a lab after the soil sample containers have been filled.

In an embodiment, the plurality of organic material samples is archived while inside the sample group box.

In an embodiment, archiving the plurality of organic material sample includes storing the plurality of organic material samples within their respective sample containers in a climate controlled environment for a period of at least 6 months.

In an embodiment, the plurality of organic material samples is archived while inside the organic material sample containers.

In an embodiment, the organic material sample comprises a soil sample. In other embodiments, the organic material comprises manure, fertilizer and/or leaves.

According to an aspect, a system for sampling and analyzing organic material is provided. The system includes: a plurality sample containers, each sample container including porous sidewalls and having a unique identifier associated therewith; a database associating, for each of the sample containers, a geographic position with the unique identifier, the geographic position corresponding to a location where an organic material sample was taken; a press for compacting organic material samples inside the sample containers, the press including at least one automated piston sized and shaped for fitting within an open-end of the sample containers; a LIBS system and a server. The LIBS system includes: a scanning device to scan the unique identifier associated with each of the plurality of sample containers; a laser head assembly and a spectrograph to analyze the organic material samples while inside the sample containers; and to generate analysis results; a processor and a memory, the memory having stored therein instructions executable by the processor to control the scanning device, the laser head assembly and spectrograph. The server includes a processor and a memory. The server is in communication with the LIBS system and the database, with the memory having stored thereon instructions executable by the processor to receive the analysis results from the LIBS system and associate the analysis results with the unique identifiers in the database.

In an embodiment, each of the plurality of sample containers includes: a body including a base and the porous sidewalls, the porous sidewalls extending peripherally from the base and defining, together with the base, a cavity with an open end for containing an organic material sample; and a removable lid covering the open end, the unique identifier being provided in at least one of the body and the lid.

In an embodiment, a thickness of the base is selected such that the base can support a weight of between approximately 15 tonnes and 30 tonnes.

In an embodiment, the system includes an oven for drying the organic material samples while inside the soil sample containers.

In an embodiment, the press is shaped and configured to receive several of said sample containers at a time.

In an embodiment, the system includes a support tray for supporting the plurality of sample containers, the tray including cavities sized and shaped for receiving the sample containers therein.

In an embodiment, the support tray includes: a base having a top side and a bottom side, the top side being provided with the cavities arranged peripherally around a central axis; and lid supports extending from the top side of the base adjacent each cavity for supporting the removable lids of the soil sample containers peripherally around the central axis, the lid supports including support arms for retaining the lids of the soil sample containers in an upright position.

In an embodiment, the tray further includes a locking mechanism for retaining the sample containers in the base of the tray.

In an embodiment, the system includes a client device in communication with the server, the client device including a processor, memory, a scanning mechanism and a geographic position sensor, the memory having stored therein instructions executable by the processor to cause the client device to scan the unique identifiers of the sample containers using the scanning mechanism, capture geographic position coordinates corresponding to a location from which an organic material sample in a corresponding sample container was taken using the geographic position sensor, and transmit the geographic position coordinates associated with corresponding unique identifiers for storage in the database.

In an embodiment, the system includes a reusable sample group box for transporting groups of sample containers to and from a lab, and for archiving groups of sample containers, the box including a plurality of slots for receiving the group of sample containers and a lid for enclosing the group of sample containers within the box.

According to an aspect, a method is provided for sampling and analyzing organic material. The method includes the steps of: (1) collecting samples of organic material; (2) tagging the samples; (3) grouping a collection of samples; (4) sending the samples to a laboratory; (5) receiving a collection of samples at a laboratory and identifying the collection; (6) drying the samples; (7) compacting the samples; (8) analyzing the samples using LIBS, or other such technology; (9) generating a report from the analyzed data; and (10) archiving the samples.

In an embodiment, the tagging of samples is done using a unique identifier, such as QR codes. Each tagged sample is further associated with indicia of source, such as the GPS coordinates of where the sample originates, or a timestamp indicating when the sample was taken.

According to an aspect, a system for containing and transporting samples is provided. The system includes porous cups for containing individual samples.

The cups can have a label affixed to the exterior displaying a unique identifier, such as a QR code or other tagging method for identifying the cup. The system also includes a shippable cardboard box adapted to receive a plurality of cups, such as twelve or twenty-four of the porous cups. The cardboard box can be further identified by a unique tag for classification and archiving.

According to an aspect, a computerized system for managing samples and manipulating analyzed data is provided. The system includes at least a server and a client device. The client device is adapted to read a tagged sample, via the unique identifier for example, and transmit to the server information to be associated with the sample. Such information may include, for example, GPS coordinates, a timestamp, or both, or the results of LIBS analysis. The server is adapted to gather data collected from the client, store it in a database, and present it in the form of a report, which can be accessible via a web browser, for example.

In an embodiment, one client device may be a mobile phone, the mobile phone being equipped with a camera, GPS receiver and mobile data connection. A user scans the QR code of a sample at the very location it was taken, while the mobile phone registers the current GPS location and sends this data to the server. A second client device may be the machine carrying out the sample analysis. The machine automatically scans a QR code and stores the analysis information in the server database along with the GPS data. Information collected by both clients can be combined to generate a report.

According to yet another aspect, a system for preparing the organic material samples for the LIBS analysis is provided. The system includes a unit for drying the samples, and a unit for compacting the samples.

BRIEF DESCRIPTION OF THE DRAWINGS

FIG. 6E is a schematic view of a pressing device according to an embodiment where the pressing device comprises a plurality of pressing heads.

FIG. 10 is a schematic illustrating a sample report generated during the method of FIGS. 1A to 1C.

DETAILED DESCRIPTION

In the following description, the term "client device" refers to any electronic device capable of executing computer code and communicating with a server via a communication channel. Examples of a client device may include, but are not limited to: a laptop or desktop computer, a tablet, or a smartphone device. The term "server" refers to a computing device capable responding to requests from a client device, by means of a communication channel. As will be evident in the remainder of the description, the server carries out a variety of functions. These functions need not be done on the same physical device, and thus the definition of a server may also refer to a collection or cluster of computing devices networked in some fashion.

What follows describes a preferred embodiment of the present invention, and provides examples for possible implementations. These are but one of many ways to implement the invention. For example, although the system and method are described in the context of soil analysis, it is appreciated that the system and method can apply to the analysis of other types of organic material. As such, the examples provided should not be taken as to limit the scope of the invention in any way. In the figures, the same numerical references refer to similar elements. Furthermore, for the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom.

A. Method

Figure 1A:
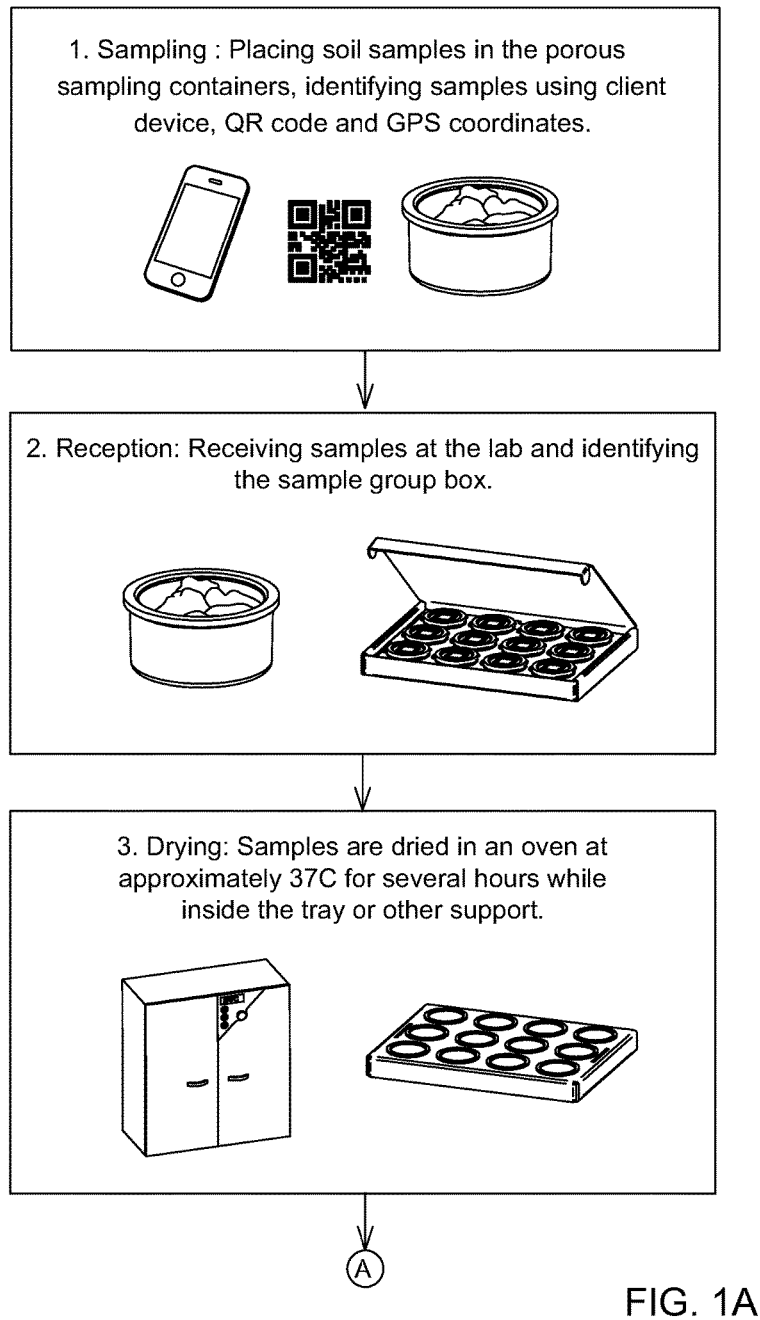
FIGS. 1A to 1C contain a flow chart schematically illustrating the steps in a method for sampling and analyzing organic material, according to an embodiment.
Figure 1B:
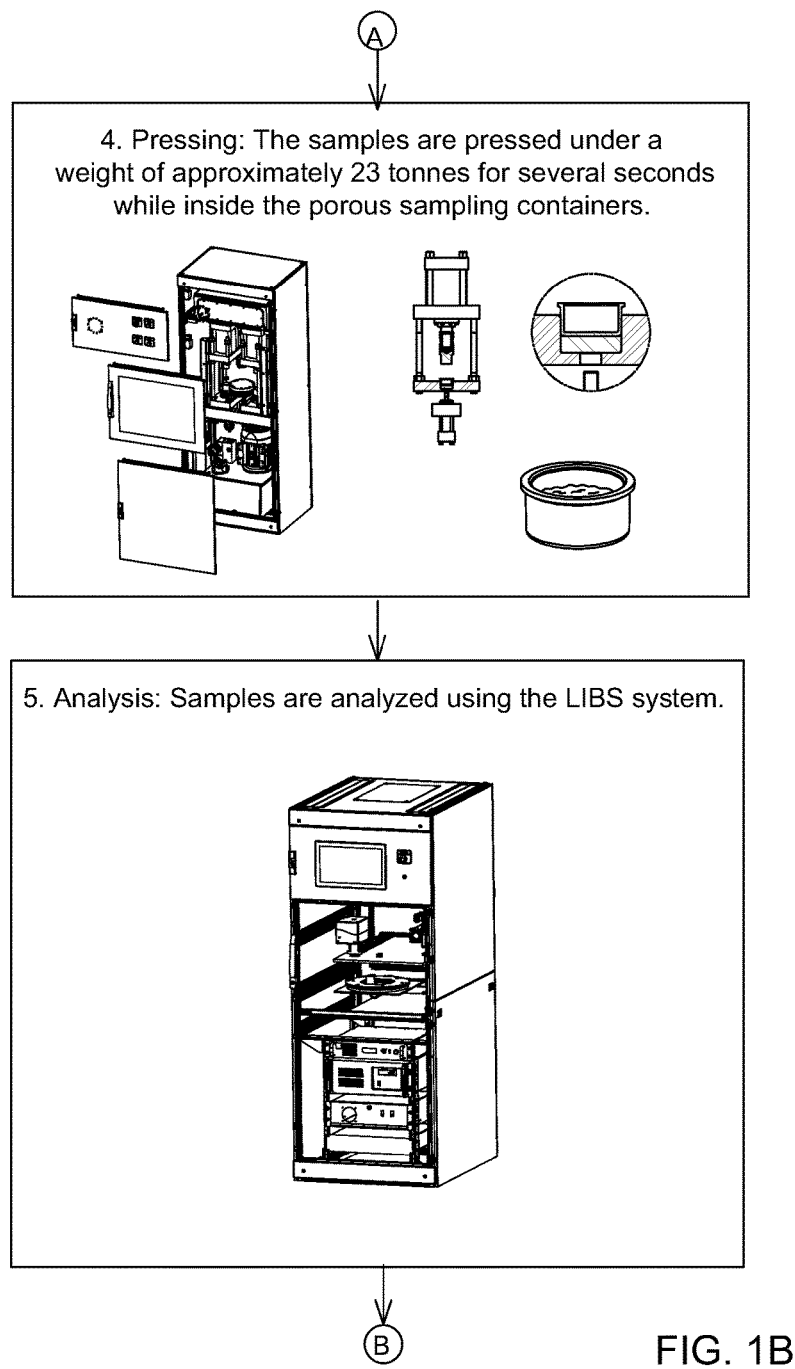
Figure 1C:
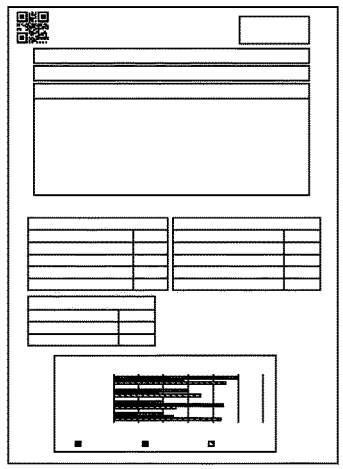
Figure 1C:
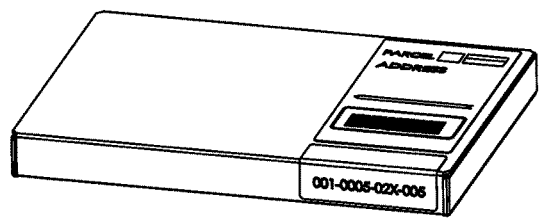
Figure 2A:
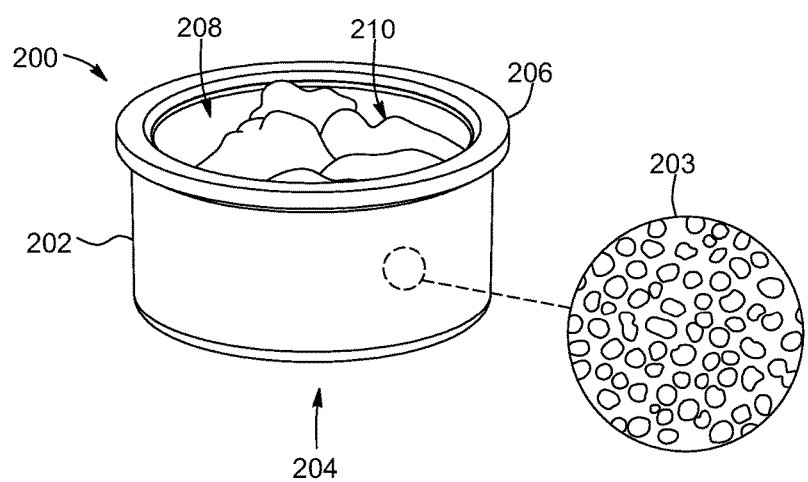
FIG. 2A is a perspective view of a sample container for use in the method of FIGS. 1A to 1C, according to an embodiment.
Figure 2B:
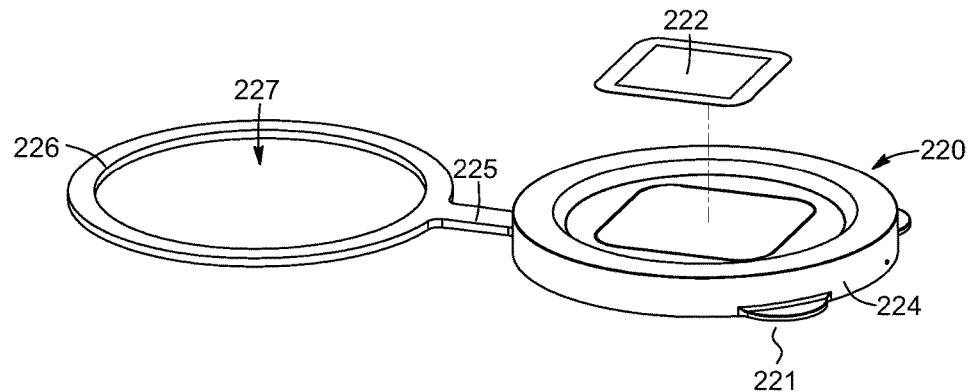
FIG. 2B is a perspective view of a container lid for sealing and identifying the sample container of FIG. 2A.
Figure 2C:
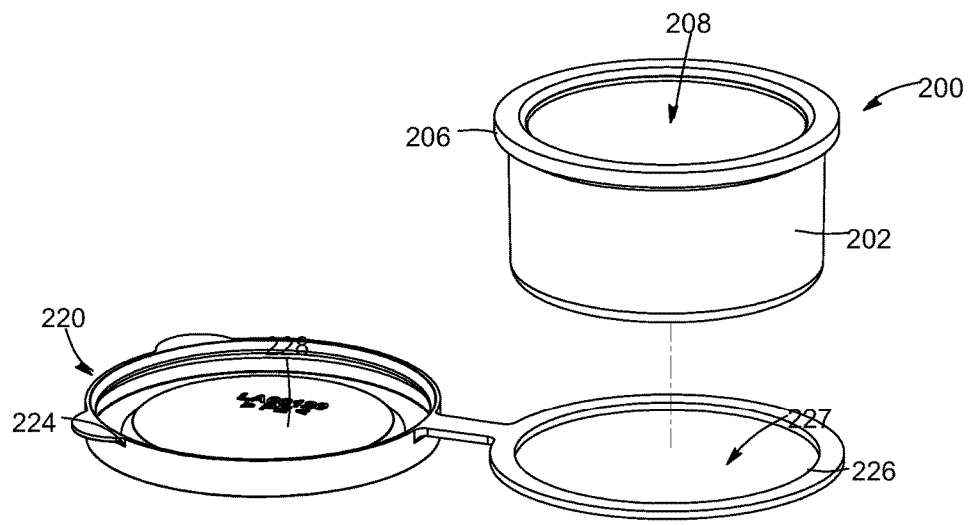
FIGS. 2C and 2D are perspective views of the sample container and lid of FIGS. 2A and 2B assembled together.
Figure 2D:
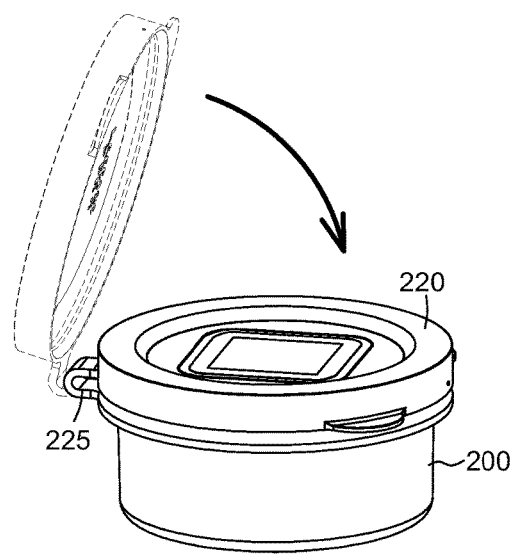

Referring to FIGS. 1A-1C, a diagram illustrating the main steps in the method of the present invention is shown, according to an embodiment. It should be understood that different steps in the method can occur in different locations. For example, some steps can occur on-site where the organic material samples are collected, and some steps can occur at a lab where the organic material samples are analyzed. It should be understood that the word "lab" is use herein to lighten the text. A "lab" can include any location on site or off site which has the necessary equipment to perform the analysis of the soil samples.

The first step comprises sampling. In this step, an agronomist, or other operator, collects samples of organic material from strategic locations across an area of land, and places them in containers which were received from a lab or other entity. In the present embodiment, the organic material samples comprise soil samples. Typically, the soil samples are collected manually, for example with a shovel or a coring tool, or with the help of a machine adapted to collect samples. In the presently described embodiment, the samples are stored in containers referred to hereinafter as "soil sample containers", as their function in this particular embodiment is to contain soil samples. However, it is appreciated that the same or similar containers can be used to contain other types of organic material, such as leave for example, and can therefore also be referred to as simply "containers" or "sample containers". In the presently described embodiment, the containers are porous sample containers. However, it is appreciated that other types of containers can also be used, such as a sealable plastic bag for example. The size of the samples can be relatively small. For example, each soil sample container can contain between 5 grams and 150 grams of soil sample. Once inside the containers, the samples are tagged according to a predetermined tagging scheme, preferably indicating where the samples originated. This step of tagging allows associating soil samples with specific geographic locations or positions on an area of land from where they were taken. This can be accomplished, for example, with the help of a client device and a QR code affixed to the soil sample container. Preferably, prior to or after filling a soil sample container, a client device is used to scan a QR code on the container and capture GPS coordinates, the GPS coordinates corresponding to where the sample was taken. The QR code and corresponding coordinate information is wirelessly transmitted and received on a server where they can be associated in a database. Once tagged, several samples are grouped together and prepared for shipping. The individual samples are packed together into a sample group box, i.e. a larger container suitable for holding a group of multiple samples, and being adapted for shipping the samples safely. The group box can also be adapted such that they identify from where the samples originate, for example by providing a label with client information. Once prepared, the group box is shipped to a lab for processing.

The second step comprises receiving the samples at the lab. The sample group box is received, and is identified according to its origin, for example using an identifier such as a QR code and/or a customer information label. This step is optional since it is possible to include customer information in the QR code on each sampling container. Tracking the sample group box when it arrives in the lab allows tracking the time between receiving a sample group box and analyzing the samples of the sample group box. When the group box is identified, the samples contained therein can be associated with a particular group, for example using the identifier or customer information. For example, a single group box can correspond to samples taken at various locations in a single field. The samples can therefore be associated to a group which corresponds to the field. The association of individual samples to a particular group can, for example, be stored in a database on a server. It should be noted that, in an embodiment, this association can be made prior to receiving the samples at the lab. For example, the lab can prepare a group box with several empty soil sample containers therein, and associate the soil sample containers with a group prior to mailing the empty soil sample containers to a client to be filled.

Once identified, the next steps involve preparing the sample for analysis. Preferably, the preparation and analysis of the sample is done in the same container in which the sample was shipped, for example to reduce the materials used and to avoid having an extra step of transferring portions of the samples to different containers. The preparation and analysis can be done with the sample inside the soil sample container in which it was shipped or, in some cases, with the sample inside the group box or the group tray in which it was shipped. In some embodiments, the soil sample containers can be transferred to a support tray which supports the samples throughout the preparation and analysis steps.

The third step comprises an optional step of drying the samples in order to prepare the samples for analysis. This can be done, for example, over the course of 12 to 18 hours at a temperature of about 37° C. in a drying chamber, such as an oven or incubator for example. The time and temperature can vary according to the sample and/or testing conditions. For example, the drying period can be anywhere between approximately 2 hours and 48 hours, and the drying temperature can be anywhere between 30° C. and 45° C. Drying is done in order to remove humidity from the samples to avoid leaching of nutrients, or water seepage in subsequent steps in which the samples are compacted and analyzed. Such effects can be avoided if, for example, the samples are dried to a humidity level of about 10% or less. In some embodiments, the drying step can be accomplished outside of the lab. For example, the samples can be dried during transport, either on their own in an ambient environment, or in a climate controlled area of a transport vehicle. In some embodiments, the soil samples can be sufficiently dried prior to arriving at the lab, and need not be dried in the oven or incubator.

The fourth step comprises pressing or compacting the samples, for example with the help of a pressing system. In this step, each sample is compressed under a weight of about 23 tonnes for several seconds. The soil is compacted to account for the fact that each sample may contain material with different characteristics. In order to get a consistent reading from each sample, they must all have a uniform surface. Compacting the soil assures that each sample is uniform. The weight applied to the samples can vary, for example according to the composition of the soil. In typical embodiments, the soil samples are pressed with a weight of between approximately 15 tonnes and 30 tonnes. Preferably, the soil samples are compacted while inside their sample containers. This provides the advantage of avoiding transferring or manipulating the soil samples. In an embodiment, each sample in a group of samples can be compacted one at a time. In an alternate embodiment, two or more samples of a group can be compacted simultaneously. Preferably, compacting a group of samples is automated. For example, the press can be configured to compact a first sample or a first set of samples, and then move the samples or the pressing head in order to continue compacting the remaining samples without manual human intervention. To aid in this task, the soil sample containers can be loaded in a support tray which allows the compacting system to more easily manipulate and reposition the soil sample containers.

Once compacted, the fifth step comprises analyzing the samples using a LIBS system. The samples can be analyzed using known LIBS analysis methods, for example the one disclosed in the international PCT application no WO 2015/077867. Preferably, the analysis is done on the samples while they are still inside their corresponding soil sample containers, and can involve shining a laser on a plurality of different areas on an exposed surface of the soil sample (i.e. the uniform surface created during the pressing step). Preferably, prior to analyzing the sample using the laser, the unique identifier of the soil sample container is scanned by the LIBS system. In this fashion, data acquired by the analysis can be associated with the sample by means of the unique identifier, for example by transmitting the analysis data to a server for storage in a database. Preferably, the analysis of a group of samples is automated. For example, the LIBS system can be configured to analyze a first sample, and then reposition the samples or the laser head in order to analyze subsequent samples without manual human intervention. To aid in this task, the soil sample containers can be loaded in a support tray which allows the LIBS system to more easily manipulate and reposition the soil sample containers. Preferably, each sample in the group is analyzed in this fashion in 60 seconds or less.

Preferably, the support tray can be provided with control samples for calibrating the LIBS system. For example, between approximately 10% and 20% of the samples being scanned can be controls. The control samples can be identified by the LIBS system by unique identifiers on their corresponding soil sample containers. In an embodiment where a group of sample comprises 12 containers, the support tray can be configured to hold 14 soil sample containers, 2 of which contain control samples.

Once the samples are analyzed, a sixth step comprises generating a report. The report can serve to present the analysis results. For example, the reports can be that from a single point of sampling, from all the sampling points, or a summary for a whole field. Preferably, the report is generated by a server connected to a database which contains the analysis results and other data associated with a sample. Preferably, the report can be accessed over the internet, for example through a web portal by a client or operator. Preferably, the report cannot be tampered with. In an embodiment, an agronomic report can be generated where recommendations are made. In such a report the client can specify report preferences which can include types of data to include in the report, and the report can be generated according to the report preferences. The recommendations can be compiled in a file readable by a fertilization device, the file providing the fertilization device with instructions to automatically distribute nutrients in a field according to the analysis results of the samples and their associated geographic locations.

A seventh step, can comprise archiving the samples. The samples can be archived inside the group box so that they can be recovered or re-analyzed at a later date. The group box can be provided with a label on a front surface, for example, so that it can be easily identified when stacked vertically, thus helping to save space. Preferably, the samples are stored for a period of at least 6 months following their analysis, according to ISO 17025 standards. The samples can be archived in a climate controlled environment, for example to avoid deterioration.

As can be appreciated, following receipt of the analysis results and/or recommendations, a fertilization plan can be developed, and this plan can be executed in order to spread the appropriate fertilizers to maintain the desired soil profile depending on the types of crops which are being grown. In an embodiment, the sampling and analysis described above can be used in the context of providing a feedback loop in the execution of a fertilization plan, and can allow for the plan to be adjusted as necessary. For example, in an embodiment, following the spreading of fertilizers, the soil can be re-sampled at similar or different locations, and the samples can be analyzed using the LIBS system in order to determine if the soil has been properly fertilized. If the soil still does not have an optimal profile, the fertilization plan can be adjusted in order to attain the desired results.

As can be further appreciated, although the method was described above in the context of soil analysis, it is understood that other types of organic material can also be analyzed. In some embodiments, fertilizer or manure can be analyzed in order to determine their authenticity. In some embodiments, the above-described system can be used in the context of foliar analysis. In such an embodiment, foliar samples can be gathered from plants and placed into sample containers. As described above, the sample containers can comprise an identifier, and the container can be associated with GPS coordinates corresponding to the location where the sample was taken. The samples can be sent to a lab where a LIBS system can analyze the composition of the foliar samples. As can be appreciated, such an analysis provides an indication of the nutrients which were actually absorbed by plants at the locations where the foliar samples were taken. An excess and/or deficiency of certain nutrients can be identified, and a fertilization plan can be developed and executed in order to correct for the excess and/or surplus. In such an embodiment, foliar analysis can be used as a feedback loop for fertilization. This can be useful, for example, in the context of agriculture or horticulture.

In some embodiments, the above-described foliar analysis can be used in combination with the above-described soil analysis. For example, the soil can be analyzed to develop a fertilization plan in preparation for cultivating a crop. After the soil is fertilized and the crops are planted, foliar samples can be taken from the crops after a determined period of time when the crops have grown. The foliar samples can thus allow verifying whether nutrients were properly absorbed by the crops. If any nutrients are missing, the soil can be re-fertilized accordingly.

As can be appreciated, different sample containers may be used depending on the type of organic material being sampled. In some embodiments, for example where it may be necessary to preserve the moisture content of the sample, a non-porous and liquid and/or airtight container may be used. In some embodiments, the container can be a bag, such as a re-sealable plastic bag, or a vessel which can be configured to contain a sample comprising fluid. It is preferred, however, that the containers each have a unique identifier which can be used to identify the samples and associate it with GPS coordinates using a mobile device, regardless of the type of container. Preferably, the containers are configured such that the samples can be prepared and analyzed using the LIBS while inside their respective container, however in some embodiments, the samples can be transferred to another container for performing the LIBS analysis.

As can be further appreciated, depending on the type of organic material being analyzed, additional or alternative steps can be used to prepare the organic material for analysis using the LIBS system. As explained above in the context of soil analysis, soil can be dried and compacted in the sample container prior to analysis using the LIBS system. However, depending on the nature of the samples of organic material, other preparatory steps may be necessary. For example, when the sampled organic material is coarse, the organic material can be crushed, ground, scrambled, blended, pulverized and/or mixed, for example to transform the sample into a more fine-grained and substantially homogeneous mixture. In some embodiments, the organic material can be dried prior to mixing and/or blending, while in other embodiments, moisture can be introduced to the sample to facilitate the blending of the sample, and the sample can be dried after the mixing and/or blending. In some embodiments, the sample may be sufficiently dense and uniform and it may not be necessary to compact the sample prior to analysis. Compacting the sample can be omitted in some further embodiments, for example if the sample has a high level of moisture or is substantially aqueous. Preferably, all the preparatory steps, including any mixing and/or blending, are performed in the sample container. However, it is appreciated that in some embodiments, some preparatory steps can involve transferring the sample to another container, for example to simplify certain preparatory steps.

Some of the preparatory steps described above can, for example, apply in the context of foliar analysis. As can be appreciated, in such a context, the samples of organic material can comprise pieces of leaves. These leaves are substantially large pieces and may not be suitable for analyzing directly using the LIBS system. Therefore, in an embodiment, after receiving foliar samples at a lab, the samples can be dried in a similar fashion as described above in the context of soil analysis. Next, the foliar samples can be reduced to a finer granularity, for example they can be crushed, blended, scrambled and/or mixed, thereby transforming the sample into a more fine-grained composition which can be substantially homogeneous. In some embodiments, the fine-grained sample can then be compacted using a pressing system, and analyzed using the LIBS system as usual.

B. System i. Soil Sample Container

With reference to FIGS. 2A to 2D, a soil sample container 200 is provided for use in the above-described method. In the illustrated embodiment, the soil sample container 200 is a sampling cup, but other shapes are also possible. The soil sample container 200 is provided with a base 204 and sidewalls 202 defining a substantially round outer contour and an inner cavity 208. The inner cavity is sized and shaped for receiving between 5 grams and 150 grams of a sample of soil 210. The upper portion of the cup is provided with a lip 206, which can serve to receive a lid, or to provide an abutment to allow the soil sample container to rest inside a support with a round cavity. Preferably, at least the sidewalls 202 or the base 204 comprise a porous material 203. The porous material 203 can be a porous plastic which allows moisture to exit the container, such as polyethylene for example with pore size diameters ranging from 7 to 150 micrometers. Preferably still, the base 204 and sidewalls 202 are sized and shaped so that they can support between at least 15 tonnes and 30 tonnes. In this configuration, the soil sample container 200 can be used to contain the sample 210 during the entire process, including the steps of drying, compacting and analyzing the sample. This eliminates the need to transfer the sample to other containers during the analysis steps, and thus reduces the steps in the overall collection/analysis process. Of course, other types of materials are also possible according to varying needs. For example, the cup could also be made out of a recyclable material. Preferably, the base 204 and sidewalls 202 are made from the same material, but in possible embodiments, the base 204 can be made of a different material which can support a higoorher load.

The soil sample container 200 can further be provided with a removable lid 220. The lid 220 comprises a cover portion which can be provided with a tag or identifier 222, such as a QR code or a barcode, for example, on an outer surface thereof. According to different possible embodiments, the lid 220 can be configured to fit inside the inner cavity 208, or can be provided with a rim 224 so that it fits around the lip 206 of the soil sample container 200. The lid serves to contain the sample 210 inside the container 200, and can also be used to identify the sample using the unique identifier 222. In the illustrated embodiment, the lid is secured to a hoop 226 via a flexible joint 225. The hoop 226 comprises a hole 227 sized to fit the container therein. In this fashion, the lid assembly can be secured to the container, while allowing the lid 220 to close by folding the cover over the flexible joint 225 and towards the hoop 226. The lib can also consist of a laminated membrane which is removably glued to the top edges of the sidewall of the container. The lid 220 may further be provided with identification information 228 on the under-side of the cover. In other embodiments, a unique identifier can be provided elsewhere in the container or in the cover. For example, a RFID chip can be affixed to the container or the cover, or embedded therein.

ii. Computer System for Identifying and Tracking Organic Material Samples

Figure 3:
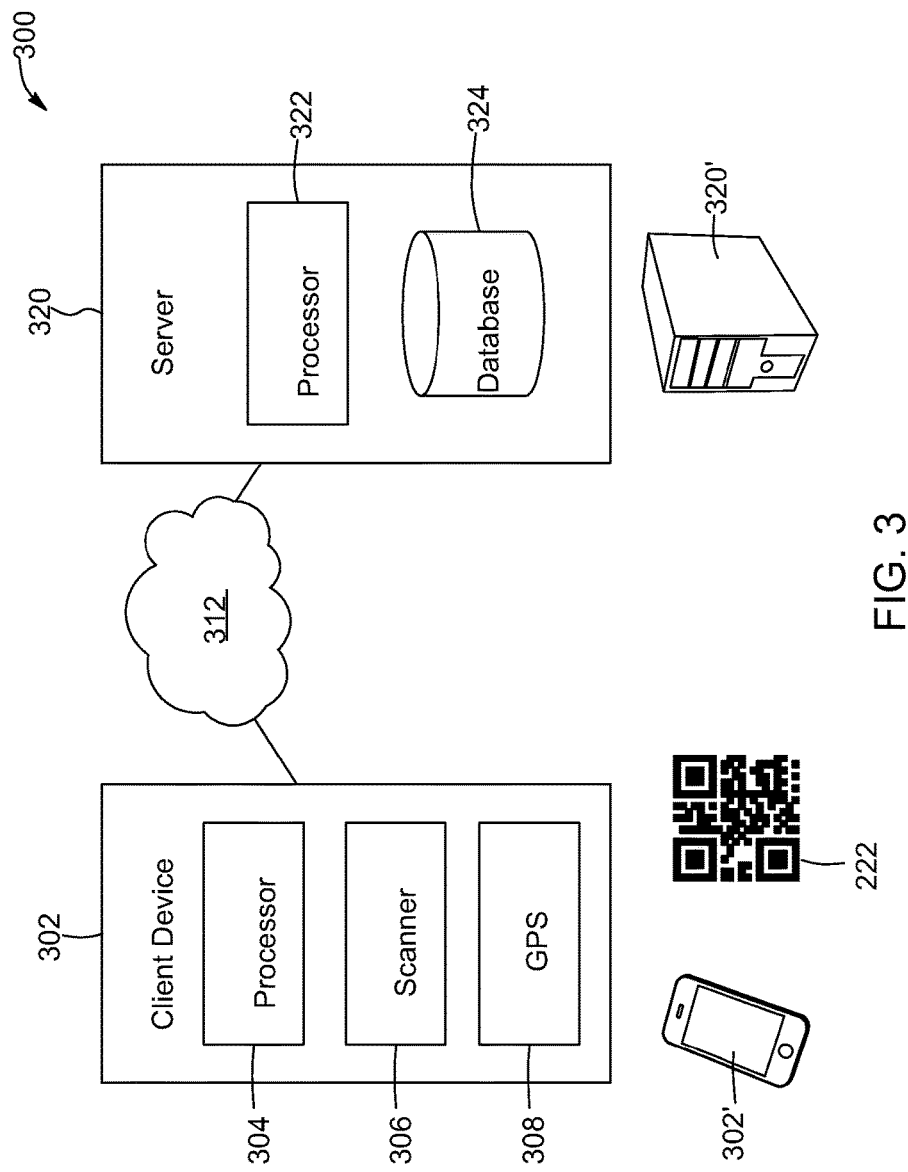
FIG. 3 is a block diagram illustrating a computer system for identifying and tracking organic material samples for use in the method of FIGS. 1A to 1C, according to an embodiment.

Referring now to FIG. 3, a computer system 300 is shown for identifying samples during the sampling step of the above-described method, and tracking the samples throughout the remaining steps. The system 300 includes a client device 302 and a server 320 which communicate via a communication channel 312. The client device 302 is preferably a mobile device 302' equipped at least with a processor 304, memory, a scanner 306 and a geolocation sensor such as GPS 308. The server 320 is equipped with at least a processor 322 and a database 324. The server can be a single computer 320' or several interconnected computers among which the processor and database are distributed.

The client device's scanner 306 can be any type of sensor which allows the client device 302 to read a unique identifier 222 associated with a sample container. For example, if the identifier 222 is a QR code, the scanner 306 can be an optical sensor or camera. If the identifier 222 is an RFID chip, the scanner 306 could be a near field communication (NFC) reader. The memory contains instructions executable by the processor 304 which allow the identifier 222 on a sample container to be scanned by the client device 302 using the scanner 306. The unique identifier 222, along with any other information relating to the sample in the sample container, such as GPS coordinates, can be transmitted to the server. The information is transmitted to the server by means of a communication channel 312, for example over the internet by a wireless data connection. It should be noted that this information need not be transmitted immediately. In some cases, for example if an internet connection is not available when the sample is scanned, the information gathered by the client device 302 can be stored on a database local to the client device 302. The client device 302 can transmit the information to the server 320 and/or synchronize information with the server 320 at a later time, for example when an internet connection 312 becomes available.

The server 320, being provided at least with a processor 322 and a database 324, can process the data received from the client 302, and store it for later access. Preferably, the server 320 can be configured to associate a unique identifier 222 with a sample and the GPS coordinates. Preferably, this association is stored within the database 324. It should be understood that, although in the illustrated figures the client device 302 only collects GPS information, other information collected by any other sensors on the client device can also be transmitted to the server and associated with the unique identifier 222 of a sample. For example, when scanning the sample, the client device 302 can also measure the current ambient temperature and record the current date and time.

Such a system can provide a simplified mechanism which allows managing large volumes of samples, and retaining information about the geographic origin of each sample. It can also simplify the sampling process by automating the gathering of information about a sample, such as its GPS coordinates for example. Of course, during the scanning step, the client 302 can transmit other information for storing on the server, such as information relating to the owner of the sample, the operator performing the sampling, or the field from which the sample was taken. The client device 302 can also generate an order form to request the analysis of the sample.

iii. Sample Group Box

Figure 4A:
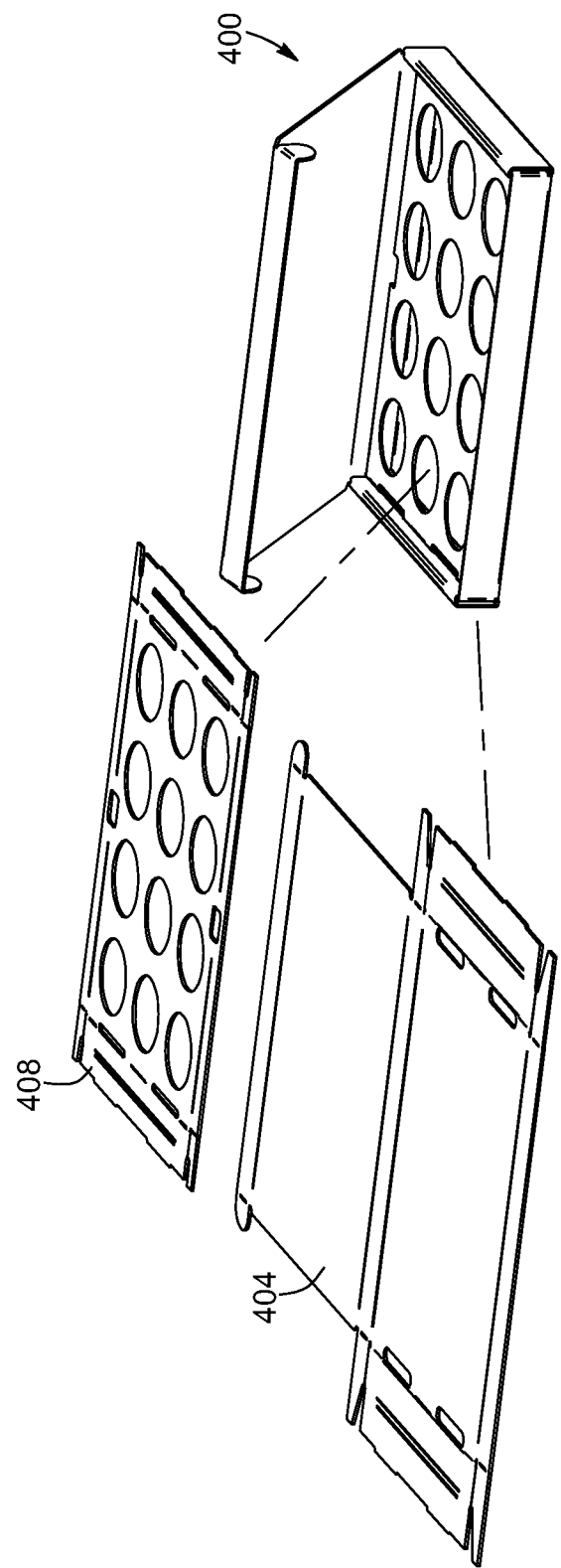
FIG. 4A is a perspective view of a sample group box for use in the method of FIGS. 1A to 1C, according to an embodiment, shown in an assembled and a disassembled configuration.
Figure 4B:
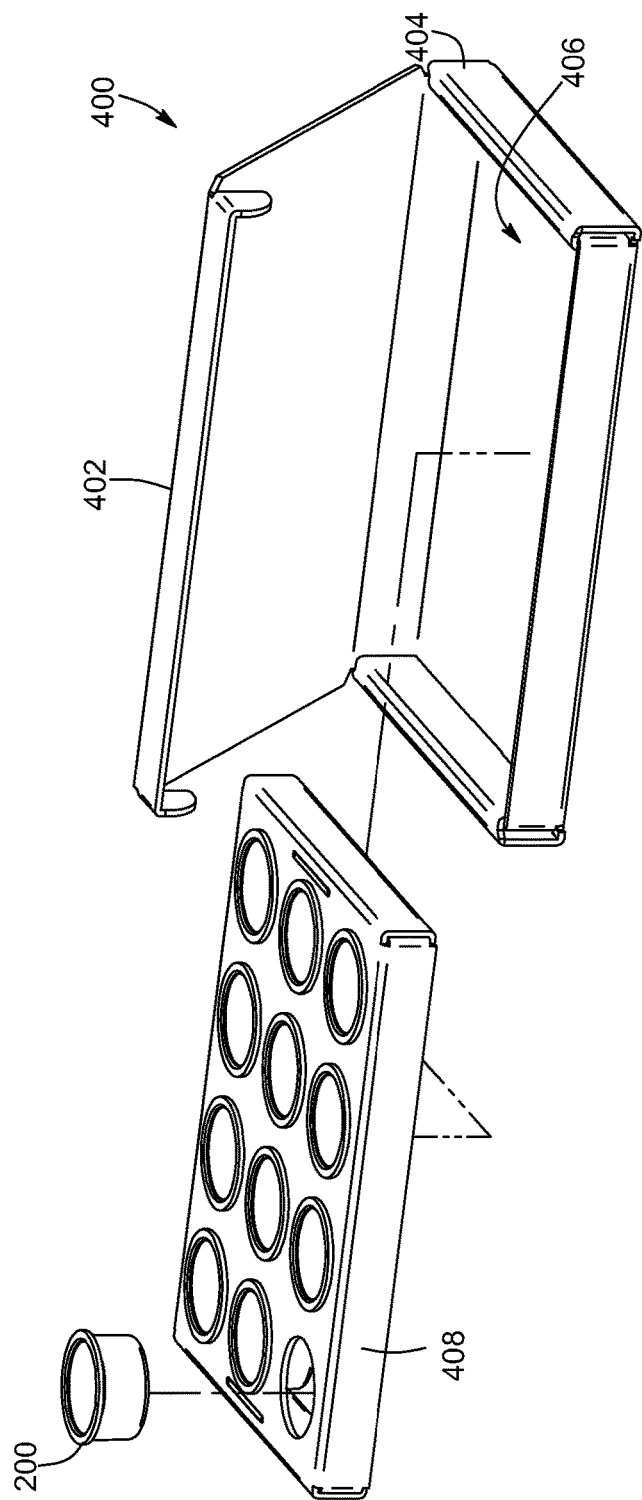
FIG. 4B is a perspective view of the sample group box of FIG. 4A in an open configuration, showing sample containers supported by a removable group tray.
Figure 4C:
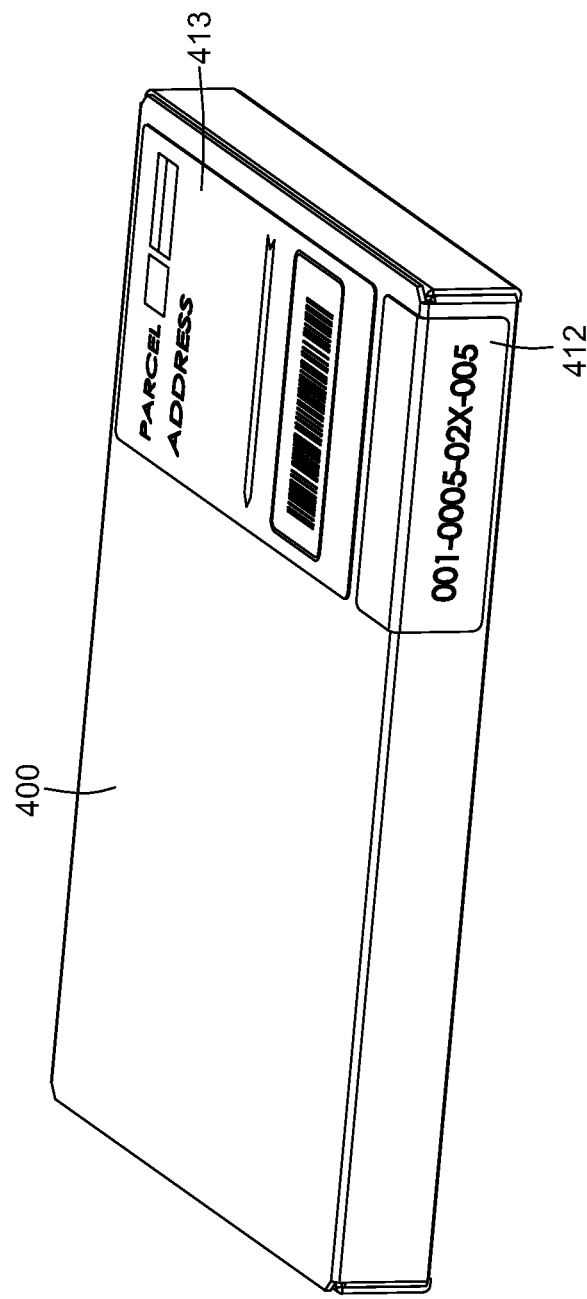
FIG. 4C is a perspective view of the sample group box of FIG. 4A in a closed configuration, showing a configuration of shipping and identification labels affixed thereto.

With reference now to FIGS. 4A to 4C, a sample group box 400 (or sample aggregation box) is shown. The sample group box 400 can serve to collect several sample containers 200 into a single container for easier transport and storage. The sample group box 400 can therefore be useful in the sampling and reception steps of the above-described method, when the samples are mailed to a lab. It can also be useful in the archiving step of the above-described method, so that the samples can be stored in a space-efficient manner for future access.

The illustrated sample group box 400 comprises a closeable lid 402 and slots 410 configured to receive sample containers 200. The group box 400 can comprise two separable components: a shell 404 and a group tray 408. The shell 404 comprises the lid 402 and a cavity 406 adapted for receiving the tray component 408 therein. As is best illustrated in FIG. 4A, the box can be assembled from flat pieces of material, such as cardboard. Of course, in other embodiments, other materials are also possible.

The closeable lid 402 allows the box 400 to be sealed, and can thus allow the group box 400 to serve as a container for shipping a group of samples. The box 400 can further be provided with labels 412, 413 to simplify the transport and identification of the box 400. For example, the box 400 can be provided with a shipping label 413 on a top surface thereof for mailing the box 400 using a parcel delivery service. The box 400 can also be provided with an identification label 412 on a side surface thereof, allowing the box 400 to be easily identified when stacked vertically among other boxes. The identification label 412 could include a unique identification number, a unique code such as a QR or barcode, or any other identification means.

An operator collecting samples can, for example, pre-pay for a group box 400. Once prepaid, the operator can receive the box 400 with the necessary labels 412, 413 affixed thereto, and with empty sample containers 200 stored therein. The operator can thus proceed with sample collection, and ship the box 400 with the samples contained therein immediately once the sampling is complete. Once the box 400 has arrived at its destination, which is typically the laboratory, the tray component 408 can be removed. Subsequent steps can be performed with the sample containers in the group tray 408, or by transferring the sample containers to another support. During the archiving step, the tray 408 can be returned to the shell 404 with the sample containers 200 stored therein. The box 300 can then be sealed for storage. The box 400 thus serves as a single container which can be used throughout the collection, analysis and archiving steps, effectively reducing the need to transfer samples and simplifying the overall process, all the while keeping groups of samples together to avoiding contamination or confusion.

Figure 4D:
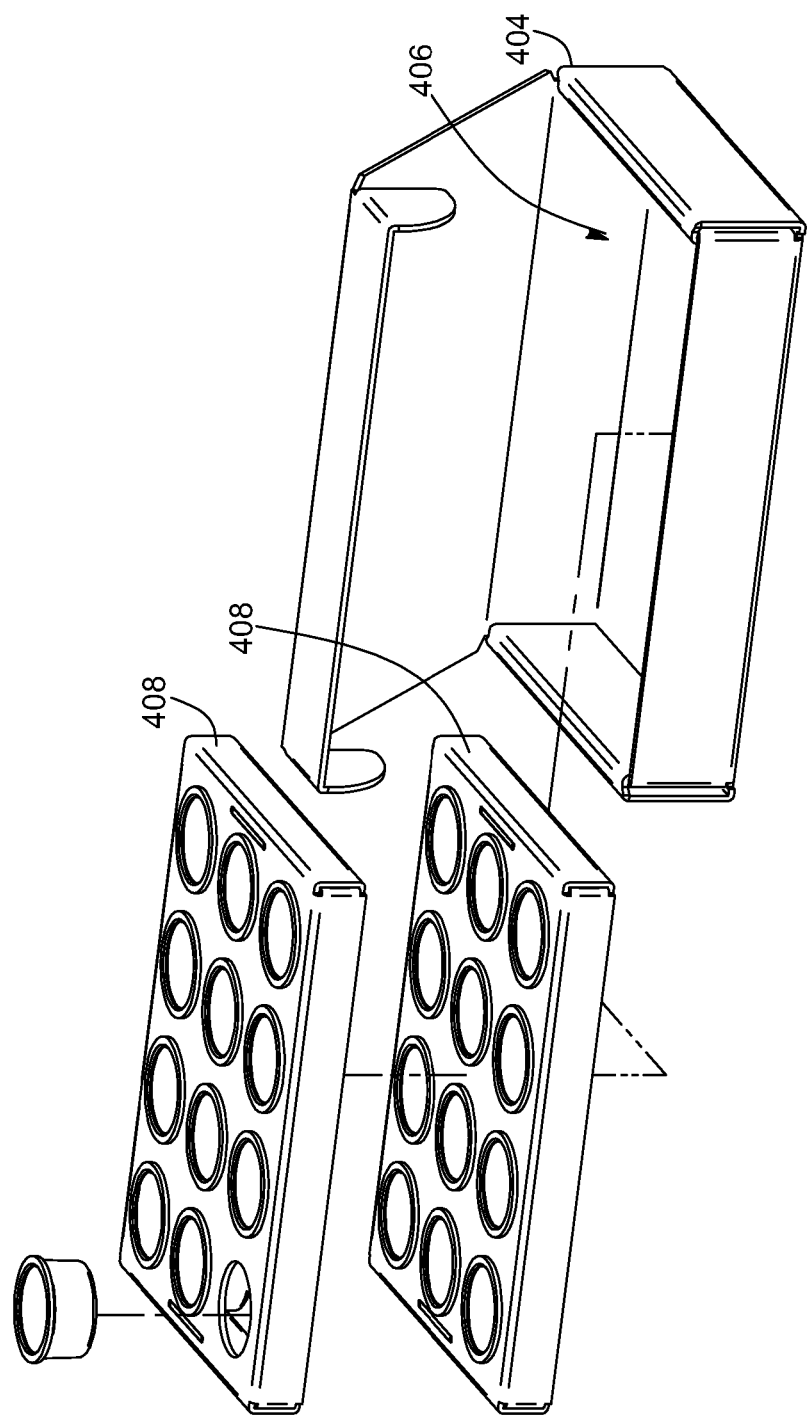
FIG. 4D is a perspective view of a sample group box for use in the method of FIGS. 1A to 1C, according to an alternate embodiment where the sample group box accommodates two removable group trays.

In the illustrated embodiment of FIGS. 4A to 4C, the box 400 is adapted to fit 12 sampling containers 200 of a single group. However, this can vary according to other embodiments. For example, as illustrated in FIG. 4D, the box 400 can be configured to accommodate 24 or more samples by layering two or more trays 408 on top of one another. This can allow, for example, for a single box 400 to store sample containers 200 from more than one group, or store sample containers 200 for a single larger group. Additionally, according to other embodiments, the box 400 can be configured differently to satisfy varying needs. For example, the trays 408 and the shell 404 can be a single unit.

iv. Drying Unit

Figure 5B:
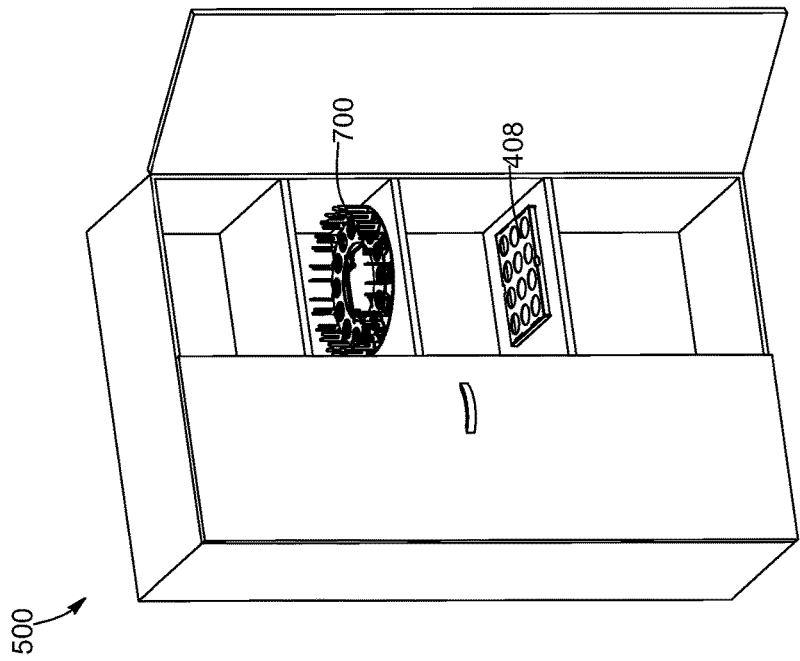
FIGS. 5A and 5B are schematic illustrations of a drying device useful during the drying step in the method of FIGS. 1A to 1C, according to an embodiment.
Figure 5A:
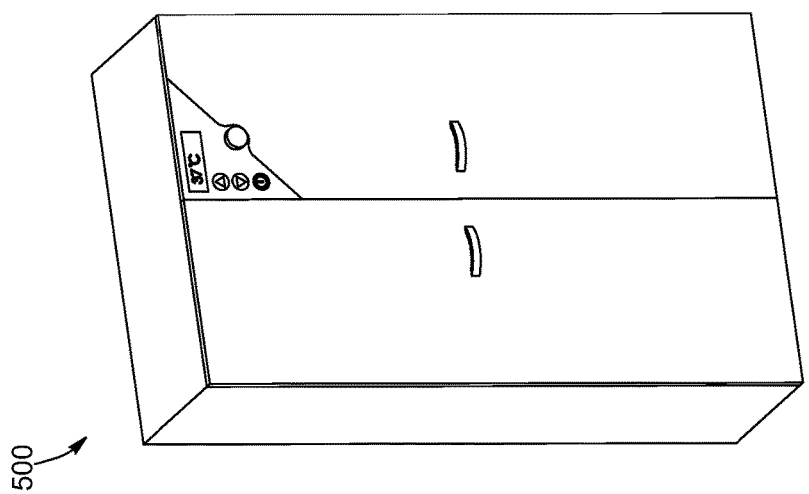

Referring now to FIGS. 5A and 5B, a drying unit 500 is shown for drying the samples during the drying step of the above-described method. In the present embodiment, the drying unit 500 is an incubator, but in other embodiments, other types of drying units are also possible, such as an oven for example. Preferably, the drying unit 500 comprises a temperature control, allowing the temperature to be maintained between approximately 30° C. and 45° C. for a period of between approximately 2 hours and 48 hours. In an embodiment, the drying unit 500 can be set at a temperature of 37° C. for 12 to 18 hours.

Preferably, the drying unit 500 is provided with supports, such as racks or shelves, for supporting sample containers which are to be dried. During the drying step, the sample containers can be placed inside the drying unit 500 while inside a support tray 700, a group tray 408, or even a group box 400. The drying unit 500 can be adapted to hold up to 120 or more trays at a time, and can be adapted to function on 208V 3-phase power.

v. Pressing System

Figure 6A:
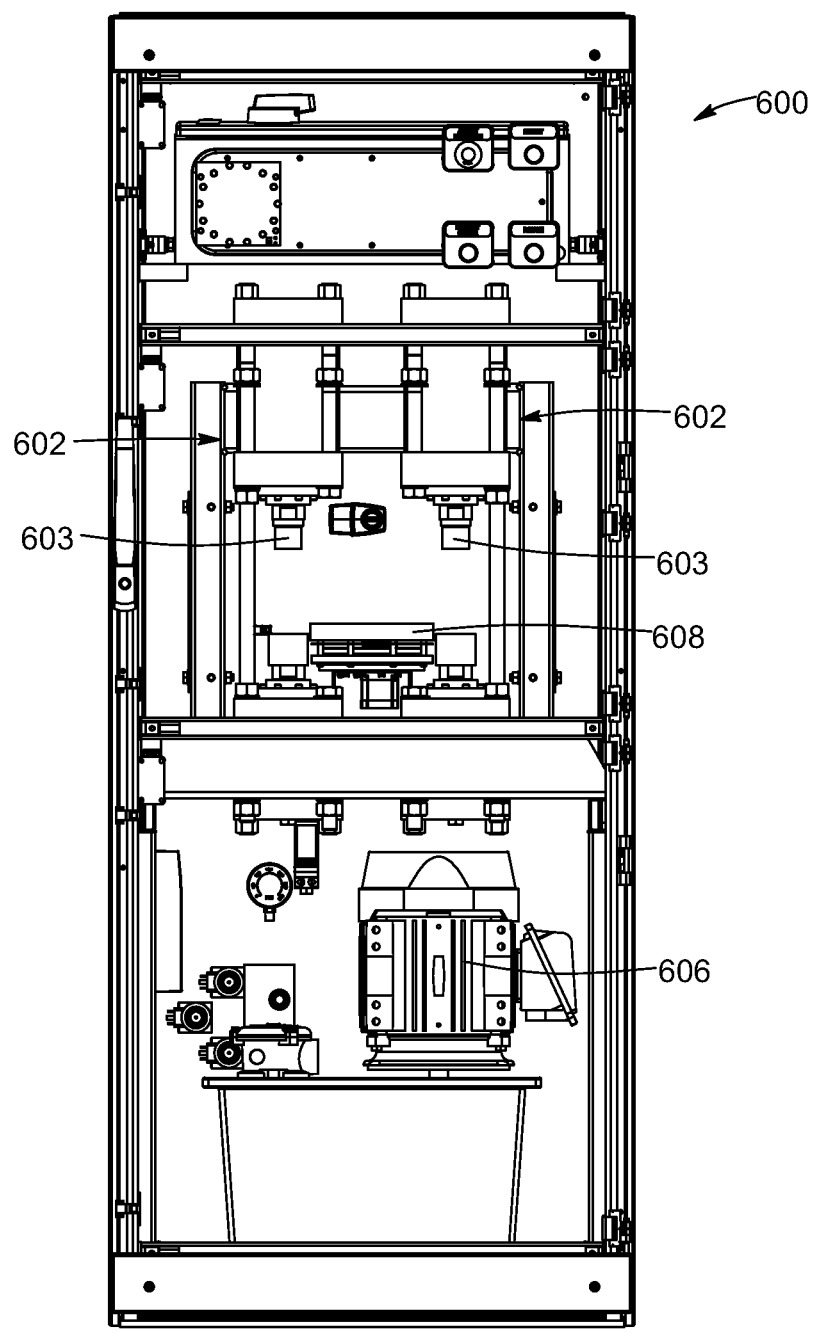
FIG. 6A is a partially transparent front view of a pressing device useful during the pressing step in the method of FIGS. 1A to 1C, according to an embodiment.
Figure 6B:
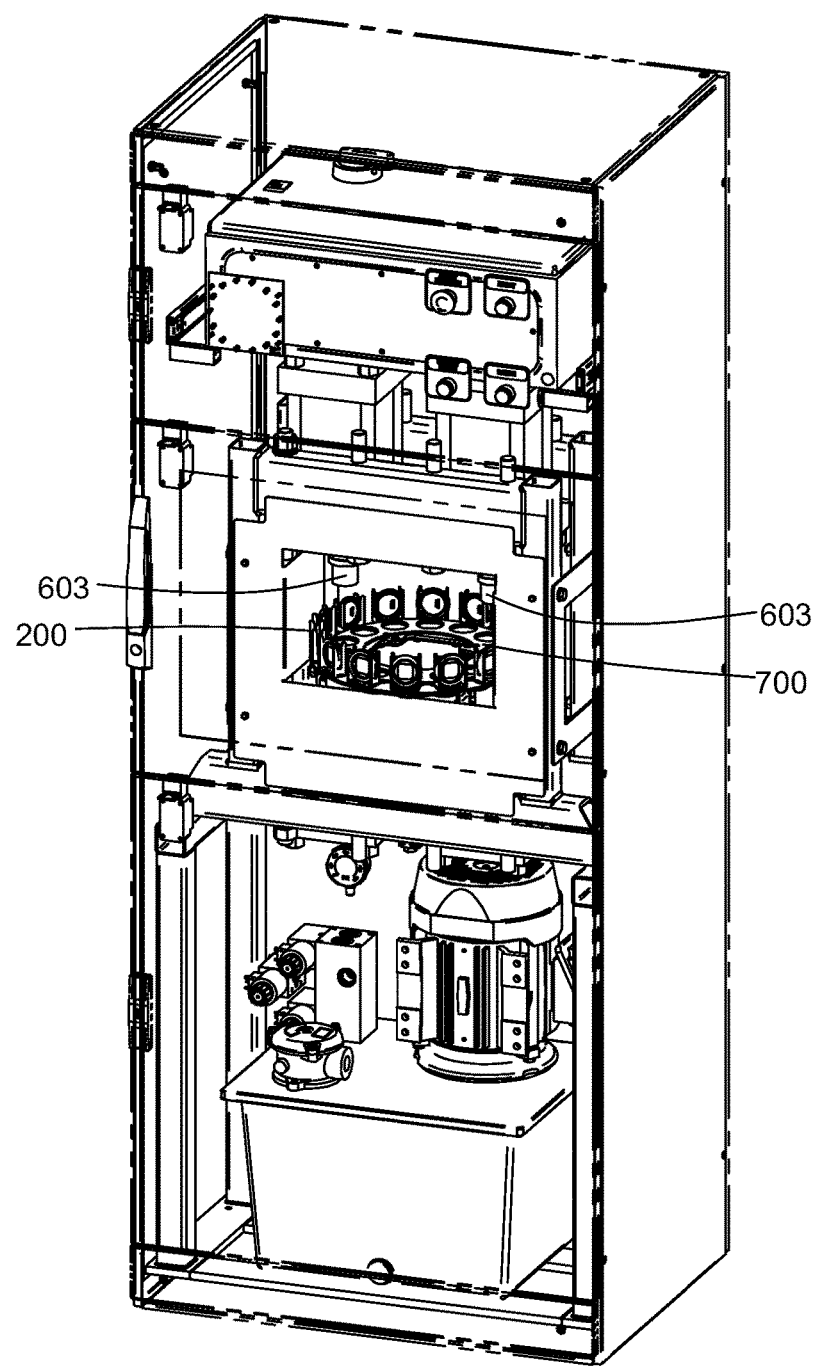
FIG. 6B is a partially transparent perspective view of the pressing device of FIG. 6A, showing a sample container support tray supported therein.

With reference now to FIGS. 6A and 6B, a pressing system 600 is shown for use in the pressing step of the above-described method. In the present embodiment, the pressing system 600 is provided with two pressing units 602 for simultaneously compacting samples in two different sample containers 200. It should be understood that in other embodiments, the pressing system 600 can be provided with one or a plurality of pressing units 602. Each pressing unit 602 comprises an automated piston which can, for example, be driven hydraulically using a motor 606. Each pressing unit is provided with a pressing head 603 sized and shaped to fit inside a sampling container and compress a sample contained therein.

Preferably, the pressing system 600 is configured to automatically compact each sample in a group of samples. In other words, the pressing system 600 can process the samples as part of a batch. In the present embodiment, the pressing system 600 is provided with a rotatable stage 608. The stage 608 can be configured to accommodate a support tray 700 which contains a plurality of sample containers. In operation, the two pressing units 602 are operated to simultaneously compact samples in two sample containers 200 opposite one another in the support tray 700. Once the first two samples have been compacted, the stage 608 is rotated, for example automatically using a motor, to position two subsequent sample containers 200 under the pressing units 602. This process is repeated sequentially until all the samples in the support tray 700 have been compacted. It should be understood that this process can vary according to the configuration of the pressing system 600. For example, if the system 600 comprises a single pressing unit 602, the samples can be compacted one at a time. In another embodiment, such as the one illustrated in FIG. 6E, a pressing unit 602 can be provided with enough pressing heads 603 to press all of the sample containers 200 at once.

Preferably, the press is configured to apply 23 tonnes of weight for 15 seconds, but this can vary according to the sample composition, tolerances of the sample containers, or preparation requirements. Typically, between 15 tonnes and 30 tonnes are applied to compress a sample. Additionally, the surface area being pressed may vary according to other embodiments. For example, the entire surface of the sample could be pressed, or only a portion of it.

Figure 6D:
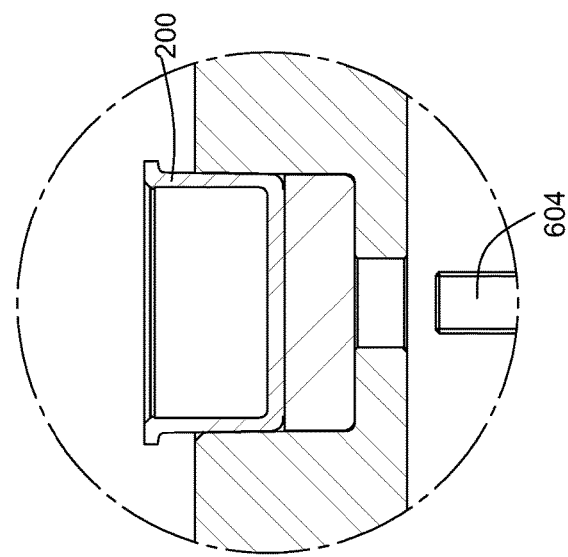
FIGS. 6C and 6D are detail views of a pressing unit, according to an embodiment where the pressing unit is provided with an ejection piston.
Figure 6C:
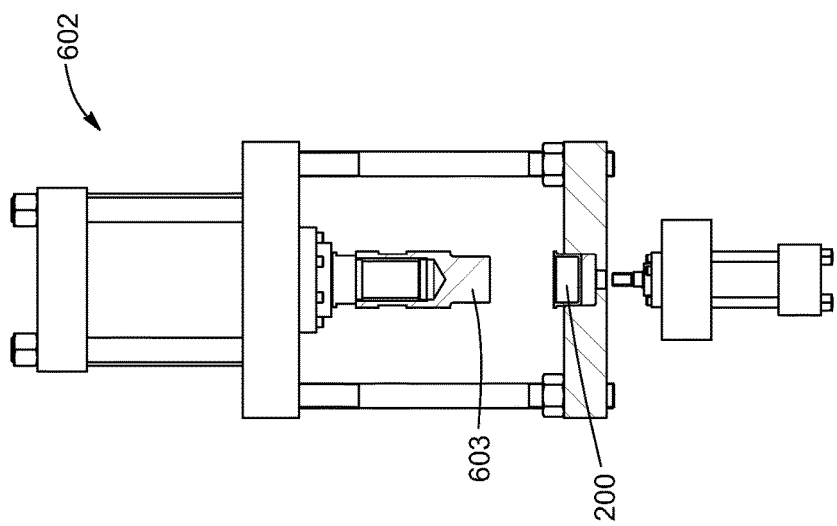

With reference to FIGS. 6C and 6D, in an embodiment, each pressing unit 602 is further provided with an ejection piston 604. Such a piston is situated below the sampling containers such that after the contents of the sampling containers have been compressed, the containers can be ejected from the pressing unit 602 by engaging the piston 604. Of course, in other embodiments, other types of ejection devices are also possible in lieu of ejection pistons 604. For example, this can be done with a burst of air through the extremities of the pressing units 602. According to other embodiments, the ejection piston may be located inside the pressing head 603.

vi. Support Tray

Figure 7A:
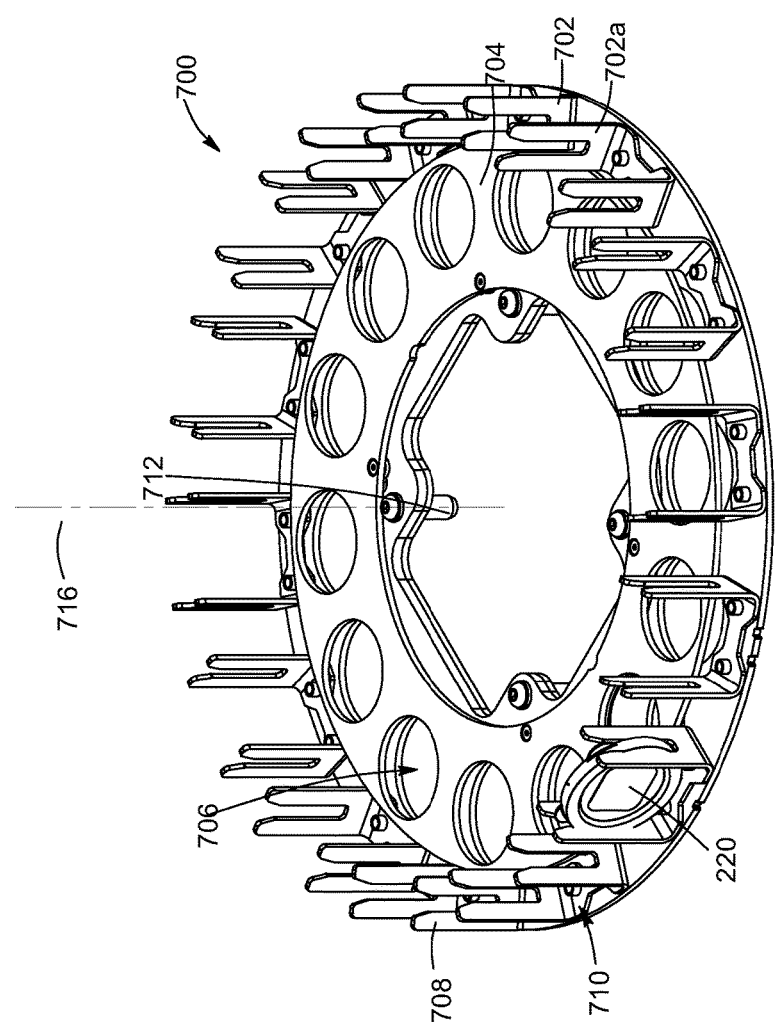
FIGS. 7A and 7B are top and bottom perspective views of a capsule support tray for use in the method of FIGS. 1A to 1C, according to an embodiment.
Figure 7B:
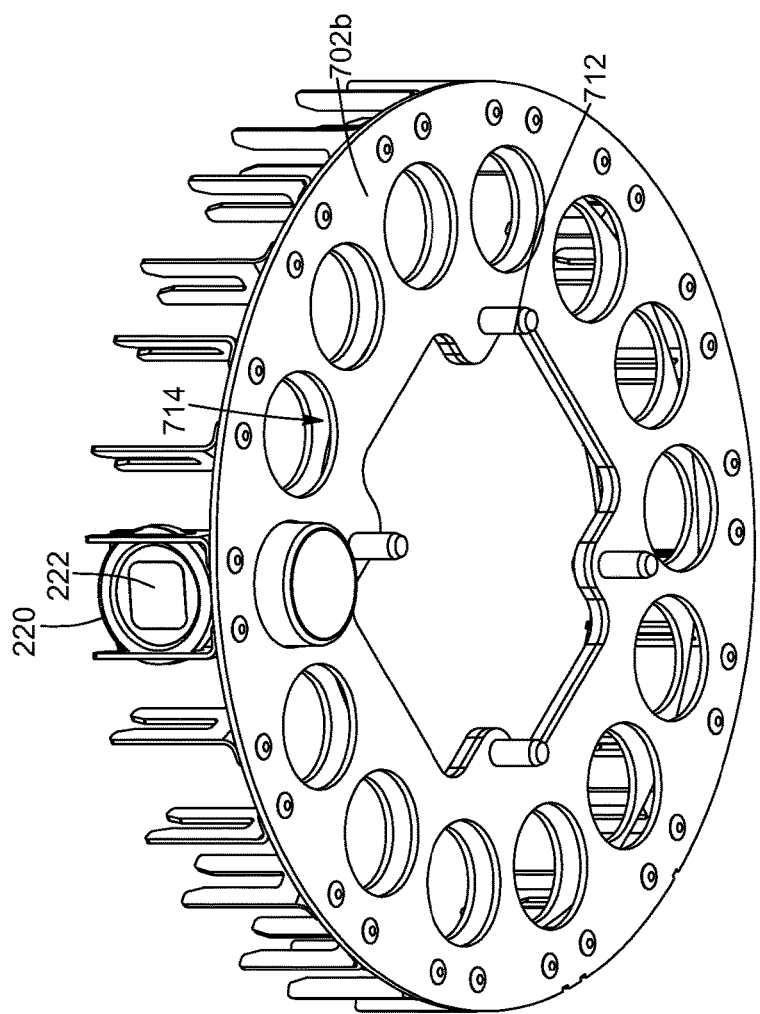
Figure 7C:
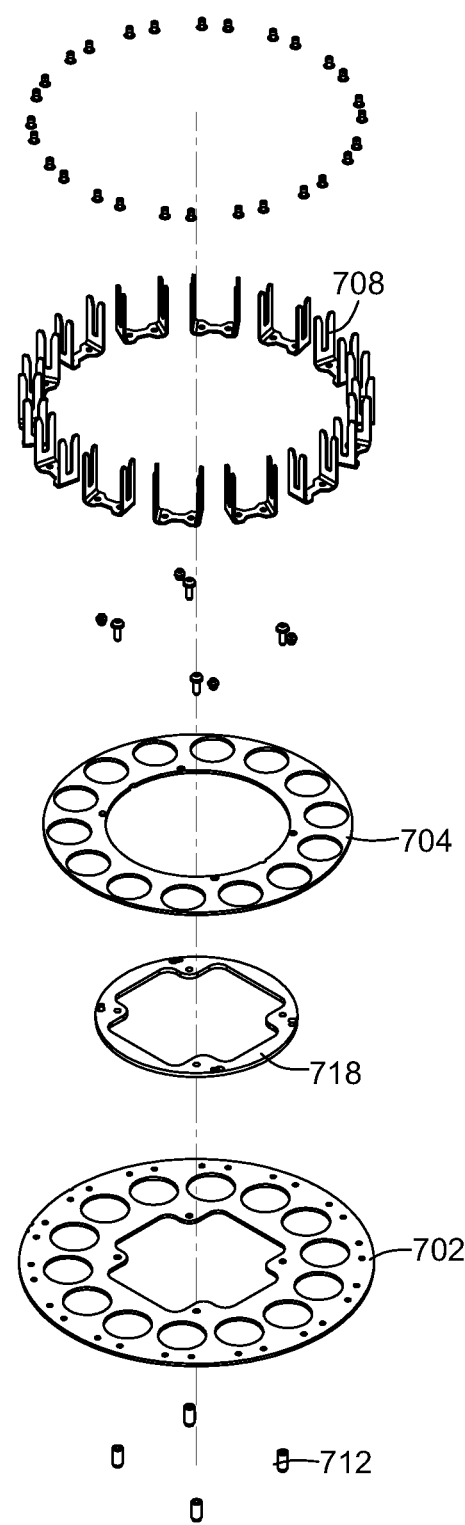
FIG. 7C is an exploded view of the capsule support tray of FIGS. 7A and 7C.

With reference now to FIG. 7A to 7C, a support tray 700 is shown for supporting a plurality of sample containers 200. The support tray 700 can simplify the above-described method by providing a means to more easily manipulate and manage a plurality of samples in several of the described steps. During the preparation step, each of the sample containers in a group can be transferred into a support tray 700. The samples can be dried, compacted and analyzed while the sample containers 200 are inside the support tray 700. In this fashion, when moving from machine-to-machine in the various steps in the method, all of the samples can be moved at once while inside the same support tray 700, effectively eliminating the need to transfer each of the sample containers 200 individually. What's more, the support tray 700 can act as an interface to aid in automating the steps of drying, compacting and analyzing. For example, the support tray 700 can be configured to be mounted to a stage within the devices used in the drying, compacting and analyzing steps, allowing those devices to more easily manipulate the sample containers without the need for human intervention.

The support tray 700 comprises cavities 706 sized and shaped for receiving sample containers therein. In the illustrated embodiment, the support tray 700 comprises a base 702 having a top side 702a and a bottom side 702b. The top side of the base 702a is provided with the cavities 706 arranged peripherally around a central axis 716. Lid supports 708 comprising lid support arms extend from the top side 702a adjacent each cavity 706. The support arms define a lid slot 710 for receiving and supporting the removable lids 220 in an upright position peripherally around the central axis 716. Preferably, the lid supports 708 are configured to support the lids 220 such that an identifier 222 on the lid 220 faces peripherally outward.

Preferably, the support tray 700 comprises a locking mechanism 704 for retaining the sample containers 200 in the base 702. In the illustrated embodiment, the locking mechanism 704 comprises a plate removably affixed to the base 702. The plate fits over the sample containers while inside the cavities 706 in the base 702, securing the containers 200 therein. The plate includes cavities which align with the cavities 706 in the base 702, allowing access to the open end of the sample containers 200 from above. A spacer 718 can be provided between the plate and the base 702

In an embodiment, the base 702 can provide additional support to the base of the sample containers 200. For example, the base can include a plate on which the base of the sample containers 200 rest. In this fashion, when the sample containers 200 are compressed, the weight can be supported by the plate. The base 702 can also be provided with feet 712 for supporting the support tray 700 at an elevation.

As can be appreciated, the described embodiment of the support tray 700 allows simplifying the manipulation and displacement of the sample containers 200 while inside the various devices used in the steps of the above-described method. For example, the support tray 700 can be removably mounted to a stage which allows the support tray 700 to be rotated or displaced within the devices, allowing the devices to position samples as required without the need for human intervention.

Figure 7D:
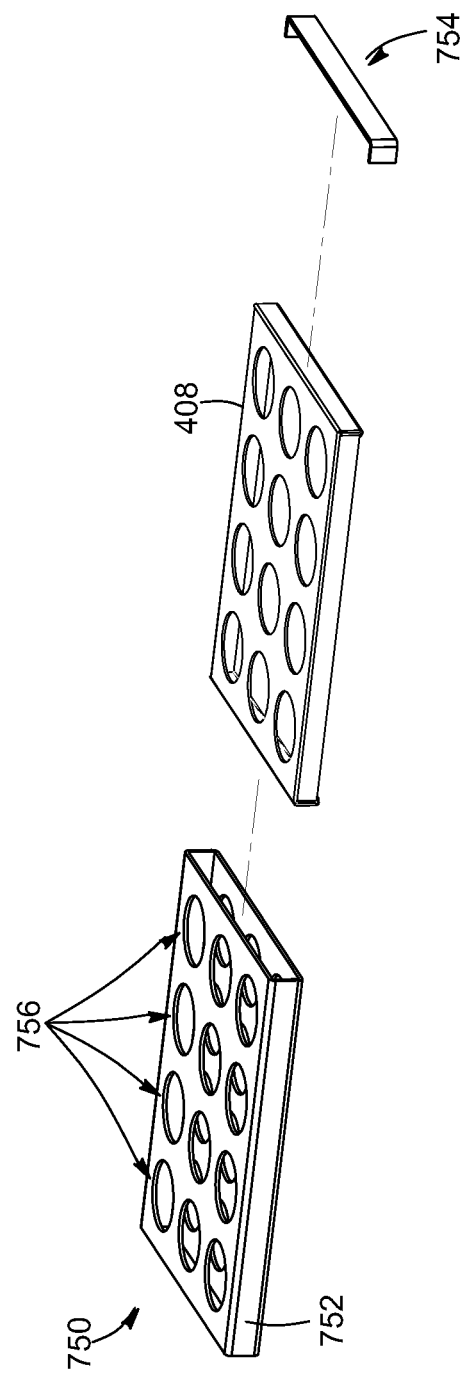
FIG. 7D is a schematic of a capsule support tray according to an alternate embodiment which supports the capsules while inside a group tray.

In an embodiment, the sample containers 200 can be placed in the support tray without leaving the group tray in which they were shipped. Referring to FIG. 7D, an alternate embodiment of a support tray 750 is shown. The support tray 750 comprises a sleeve 752 and a handle 754. The sleeve 752 is adapted to receive a single group tray 408, and is provided with holes 756 aligned above each sample container 200 in the tray 408, such that the samples are accessible from above. In the present embodiment, the sleeve 752 is comprised of metal; however, the material may vary according to other embodiments. The handle 754 encloses the tray 408 in the sleeve 752, such that the ensemble forms a drawer which can fit inside a LIBS system or a pressing system, and can be moved as needed along X and Y axes.

vii. LIBS System

Figure 8B:
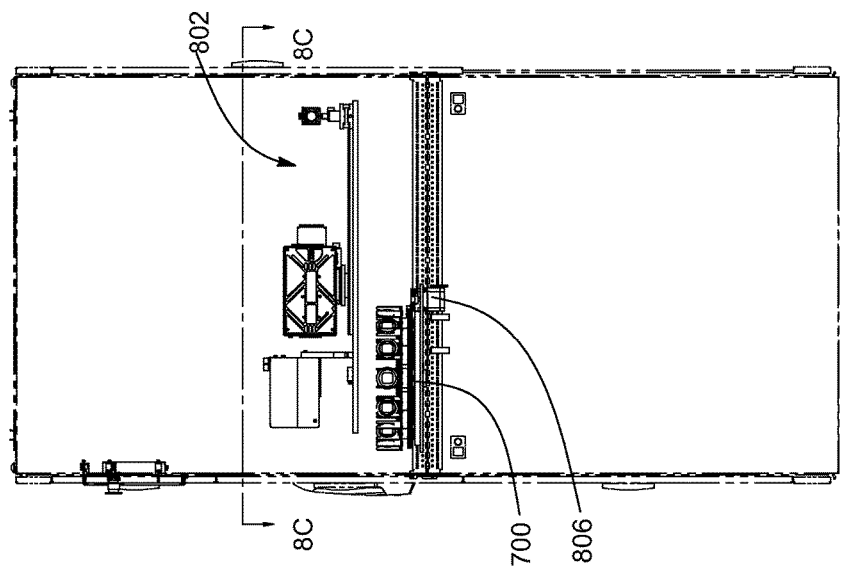
FIG. 8B is a partially transparent side view of the LIBS system of FIG. 8A.
Figure 8A:
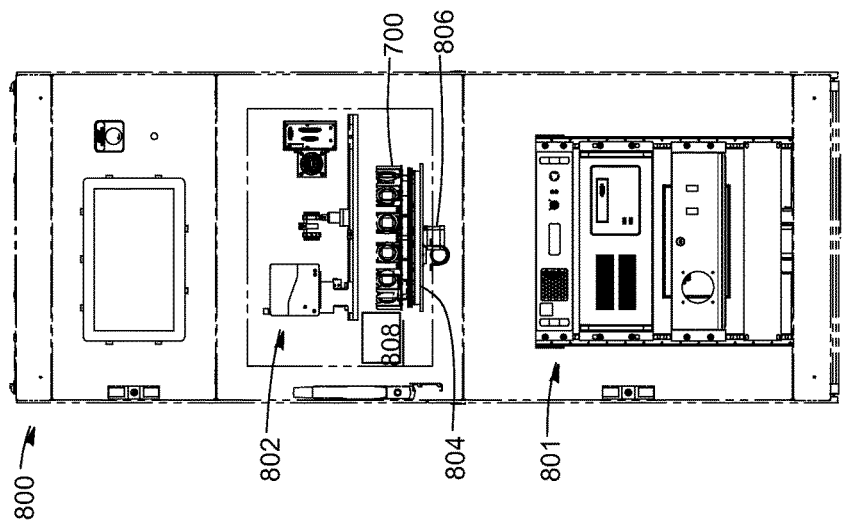
FIG. 8A is a partially transparent front view of a LIBS system for use in the method of FIGS. 1A to 1C, according to an embodiment.
Figure 8C:
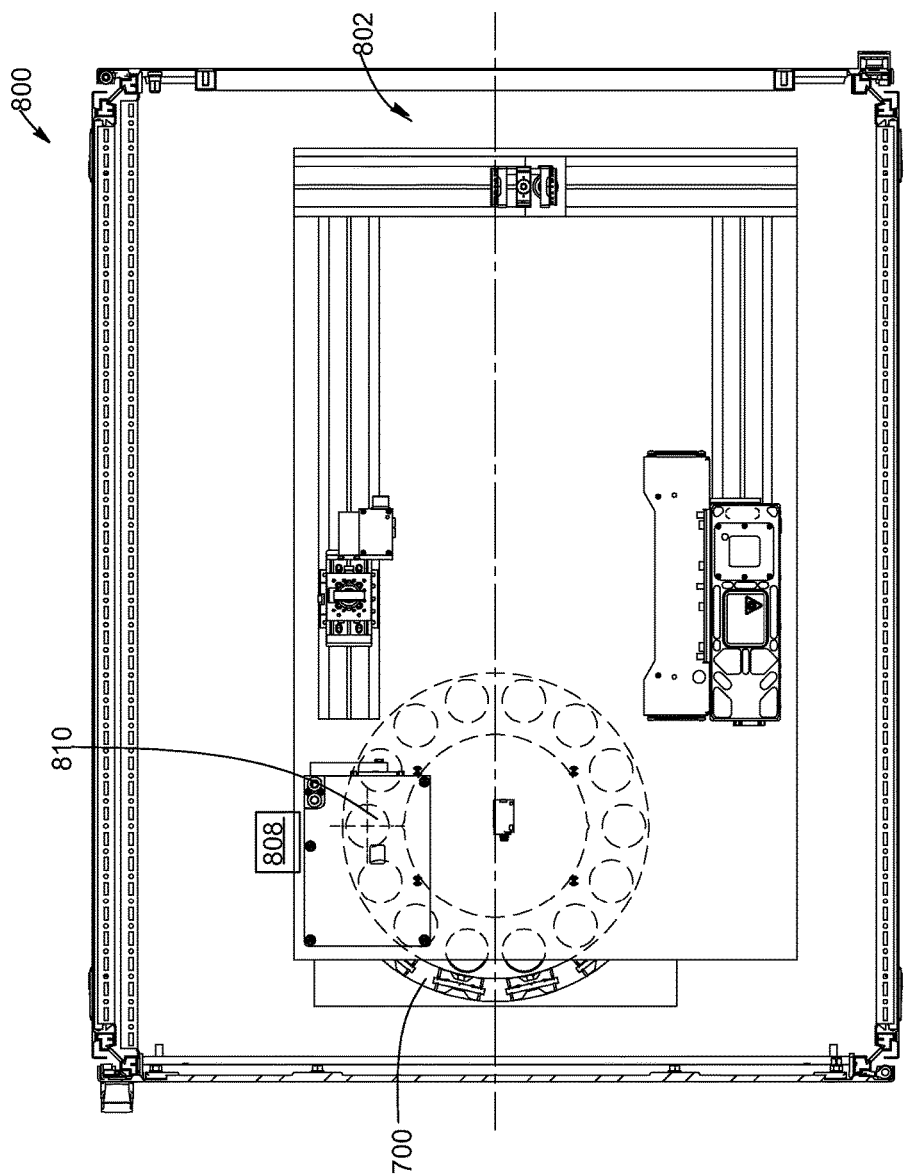
FIG. 8C is a cross-sectional view of the LIBS system of FIG. 8B taken along line 8C-8C.

Referring to FIGS. 8A to 8C, a LIBS system is shown 800 for use during the analysis step of the above-described method. The LIBS system 800 comprises a laser head assembly and spectrograph 802 to analyze samples while inside their sample containers 200, a scanning device 808 to scan the unique identifier associated with each sample, and a computing system 801 comprising at least a processor and memory. The LIBS system 800 also comprises a stage 804 for accommodating a support tray 700. The support tray 700 can be rotated or displaced using a motor 806 or actuator, for example.

Figure 9:
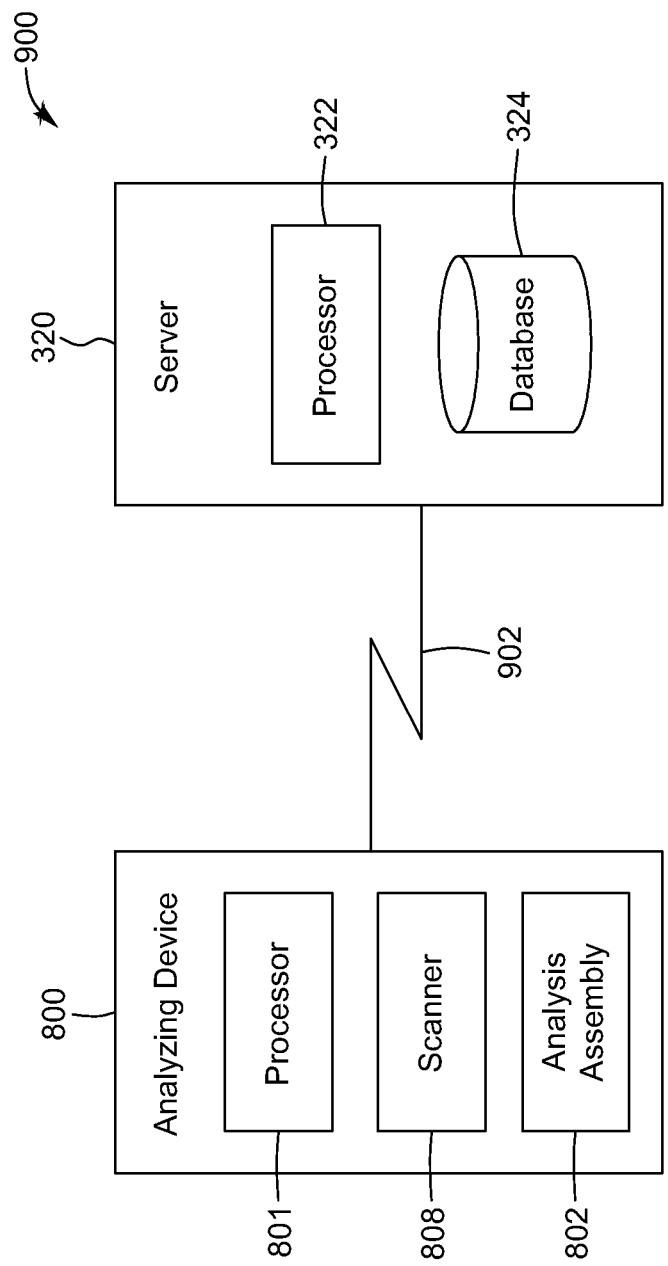
FIG. 9 is a block diagram illustrating a computerized system for identifying and analyzing organic material samples for use in the method of FIGS. 1A to 1C, according to an embodiment.

In operation, the LIBS system 800 is controlled by the computing system 801 to identify an individual sample 810 by reading the unique identifier (i.e. barcode, QR code, etc.) on the sample container 200 using the scanning device 808. The scanning device 808 can comprise any type of sensor capable of reading the unique identifier. For example, if the unique identifier is a QR code, the scanning device can comprise an optical sensor or a camera. Once the identifier is scanned, the system 801 can direct the laser head assembly and spectrograph 802 to perform an analysis on the sample 810 in the container and generate analysis results. Preferably, analyzing the sample and generating the analysis results is performed in 60 seconds or less. Once the analysis of a sample is complete, the system 801 can operate the stage 804 to move another sample container 200 into position for analysis. This can be repeated until each of the samples has been analyzed, thus allowing all the samples to be analyzed sequentially without manual human intervention. In other words, the LIBS system 800 can process the samples as part of a batch. The system 801 can be configured to only read an identifier if a sampling cup is present in the slot to be analyzed. If a sample is missing from a particular slot, or if the sample is up-side down, the system 801 can skip the analysis for that slot.

viii. Computer System for Analyzing Samples, Storing Results and Generating Reports With reference now to FIG. 9, an overview of a computer system 900 for analyzing samples, storing analysis results, and generating reports is shown. The system 900 comprises the analysis device 800 (i.e. the LIBS system) and the server 320 in communication via a communication channel 902. In operation, the processor 801 in the LIBS system 800 transmits to the server 320 the results from an analysis of a sample, along with the sample's identification information (read via the scanner 808). The data can be transmitted to the server via a communication channel 902, such as over the internet, wide area network or local area network, depending on where the server 320 is physically located relative to the LIBS system 800. The server 320 can then store the analysis information and associate it with the identified sample in the database 324, along with the information collected about the sample during the sampling step in the above-described method (such as the GPS location information).

The analysis results, tagging/identification information, and any other information stored in the server's database 324 can be used to generate a report. A sample of such a report is shown in FIG. 10. The report may include details about the analysis of a single sample, or may collect data from several samples to help in developing an agro-environmental fertilization plan. This report can be accessed, for example, by communicating with the server over the internet. In such a fashion, an operator who ordered the analysis of samples will be able to consult the analysis report by visiting a web-page on the internet, immediately after the analysis has been completed. The operator could also specify report preferences, and the server can use these preferences in order to generate a report which displays certain information according to the preferences. Information in the report may include the pH level of the sample, and the concentration of various minerals such as potassium, phosphorus, magnesium, aluminum and calcium, among others. Such information can be presented, for example, by using tables or graphs. The report can also include indications to identify the report, in addition to indications to identify the sample, by using a QR code for example. The report can further include information for identifying the operator who ordered the report, information to identify the person who carried out the analysis, and information relating to how the analysis was performed.

As is evident from the present disclosure, the method and systems described herein provide a streamlined process for gathering and analyzing soil samples and/or samples of other types of organic materials. A single container is used to collect, ship, and analyze samples, eliminating the need to transfer the samples to different containers several times during the process, as is the case in the prior art. Additionally, the present invention provides a solution for using LIBS technology, or the like, in the context of analyzing soil from many samples, possibly across several fields, and provides a method to easily manage and access information relating to the analysis. It further allows analyzing soil in a fashion which does not destroy the samples, thus permitting repeated analyses if necessary. Finally, the method and system provide a simplified means for ordering soil analysis by an operator. The operator need only order a pre-paid box, tag samples, and ship the box. Once the analysis is complete, the operator can immediately consult a report over the internet. This removes a significant amount of paper from the process, and automates the organization and management of analysis data.

The invention claimed is:

1. A method for sampling and analyzing organic material comprising the steps of:
 a) providing a sample container having sidewalls defining a cavity for receiving an organic material sample therein, and having a unique identifier associated therewith;
 b) associating, on a database, a geographic position with the unique identifier, the geographic position comprising geographic coordinates corresponding to a location where the organic material sample was taken;
 c) receiving the sample container with the organic material sample contained therein;
 d) compacting the organic material sample while inside the sample container;
 e) analyzing the compacted organic material sample using a Laser Induced Breakdown Spectroscopy (LIBS) system and generating analysis results; and
 f) associating, on the database, the analysis results with the unique identifier of the sample container.

2. The method according to claim 1, further comprising the step of drying the organic material sample while inside the sample container below a humidity level of approximately 10%.

3. The method according to claim 2, wherein drying the organic material sample comprises heating the organic material sample inside an oven at a temperature between approximately 30° C. and 45° C. for a period of between approximately 2 hours and 48 hours.

4. The method according to claim 1, wherein compacting the organic material sample comprises hydraulically pressing the organic material sample with a weight of between approximately 15 tonnes and 30 tonnes.

5. The method according to claim 1, wherein the organic material sample contained in the sample container is between approximately 5 grams and 150 grams.

6. The method according to claim 1, wherein in step e), a plurality of organic material samples are analyzed sequentially as part of a batch, each of the plurality of organic material samples being provided in individual sample containers having respective unique identifiers.

7. The method according to claim 1, wherein step e) of analyzing the organic material sample is performed in less than 60 seconds.

8. The method according to claim 6, wherein the batch comprises at least one control sample for calibrating the LIBS system.

9. The method according to claim 6, wherein between approximately 10% and 20% of the organic material samples in the batch are control samples.

10. The method according to claim 6, wherein in step d), the plurality of organic material samples are compacted sequentially as part of the batch.

11. The method according to claim 6, comprising a step of loading the plurality of organic material samples in a tray, at least one of steps d) to f) being performed while the organic material samples are in the tray.

12. The method according to claim 1, wherein step e) comprises a sub-step of scanning the unique identifier within the LIBS system prior to performing the analysis of the organic material sample.

13. The method according to claim 1, wherein analyzing the organic material sample using the LIBS system comprises shining a laser on a plurality of different areas on an exposed surface of the organic material sample.

14. The method according to claim 1, further comprising the steps of receiving report preferences from a user and generating a report summarizing the analysis according to the report preferences.

15. The method according to claim 1, further comprising the step of grouping a plurality of sample containers in a sample group box and mailing the sample group box via a postal service.

16. The method according to claim 15, further comprising the step of providing the sample group box with a pre-paid postage label for returning the sample group box to a lab after the sample containers have been filled.

17. The method according to claim 15, wherein the plurality of organic material samples is archived while inside the sample group box.

18. The method according to claim 15, wherein archiving the plurality of organic material sample comprises storing the plurality of organic material samples within their respective sample containers in a climate controlled environment for a period of at least 6 months.

19. The method according to claim 15, wherein the plurality of organic material samples is archived while inside the sample containers.

20. The method according to claim 1, wherein the sample container provided in step a) has porous sidewalls.

21. The method according to claim 1, wherein the organic material sample taken in step b) comprises soil.

22. The method according to claim 1, wherein the organic material sample taken in step d) comprises at least one of: leaves, fertilizer, and manure.

23. The method according to claim 1, further comprising a step of mixing or blending the organic material sample prior to step e).

24. The method according to claim 1, further comprising a step of reducing a particle size of the organic material sample prior to step e).

25. A system for sampling and analyzing organic material comprising:
a plurality sample containers, each sample container having sidewalls defining a cavity with an open end for receiving a corresponding organic material sample therein, and having a unique identifier associated therewith;
a database associating, for each of the sample containers, a geographic position with the unique identifier, the geographic position comprising coordinates corresponding to a location where the corresponding organic material sample was taken;
a press for compacting organic material samples while inside the sample containers, the press comprising at least one automated piston sized and shaped for fitting within the open-end of the sample containers;
a LIBS system comprising:
a scanning device to scan the unique identifier associated with each of the plurality of sample containers;
a laser head assembly and a spectrograph to analyze the compacted organic material samples; and to generate analysis results;
a processor and a memory, the memory having stored therein instructions executable by the processor to control the scanning device, the laser head assembly and spectrograph and;
a server comprising a processor and a memory, the server being in communication with the LIBS system and the database, the memory having stored thereon instructions executable by the processor to receive the analysis results from the LIBS system and associate the analysis results with the unique identifiers in the database.

26. The system for sampling and analyzing organic material according to claim 25, wherein the plurality of sample containers each comprise:
a body comprising a base and the sidewalls, the sidewalls being porous sidewalls extending peripherally from the base and having a thickness extending between the cavity and an exterior of the sample container; and
a removable lid covering the open end, the unique identifier being provided in at least one of the body and the lid.

27. The system for sampling and analyzing organic material according to claim 26, wherein a thickness of the base supports a weight of between approximately 15 tonnes and 30 tonnes.

28. The system for sampling and analyzing organic material according to claim 25, further comprising an oven for drying the organic material samples while inside the sample containers.

29. The system for sampling and analyzing organic material according to claim 25, wherein the press is shaped and configured to receive several of said sample containers at a time.

30. The system for sampling and analyzing organic material according to claim 25, further comprising a support tray for supporting the plurality of sample containers, the support tray comprising cavities sized and shaped for receiving the sample containers therein.

31. The system for sampling and analyzing organic material according to claim 25, wherein the support tray comprises:
a base having a top side and a bottom side, the top side being provided with the cavities arranged peripherally around a central axis;
lid supports extending from the top side of the base adjacent each of the cavities for supporting the removable lids of the sample containers peripherally around the central axis, the lid supports comprising support arms for retaining the lids of the sample containers in an upright position.

32. The system for sampling and analyzing organic material according to claim 25, wherein the support tray further comprises a locking mechanism for retaining the sample containers in the base of the tray.

33. The system for sampling and analyzing organic material according to claim 25, further comprising a client device in communication with the server, the client device comprising a processor, memory, a scanning mechanism and a geographic position sensor, the memory having stored therein instructions executable by the processor to cause the client device to scan the unique identifiers of the sample containers using the scanning mechanism, capture geographic position coordinates corresponding to a location from which a sample in a corresponding sample container was taken using the geographic position sensor, and transmit the geographic position coordinates associated with corresponding unique identifiers for storage in the database.

34. (The system for sampling and analyzing organic material according to claim 25, further comprising a reusable sample group box for transporting groups of sample containers to and from a lab, and for archiving groups of sample containers, the box comprising a plurality of slots for receiving the group of sample containers and a lid for enclosing the group of sample containers within the box.

35. A method for analyzing samples of organic material, the method comprising the steps of:
   a) storing, on a database, geographic positions and unique identifiers, the unique identifiers uniquely identifying the samples, the geographic positions comprising geographic coordinates corresponding to locations where the samples of organic material were taken;
   b) receiving the samples of organic material;
   c) compacting the samples of organic material;
   d) analyzing the compacted organic material sample using a Laser Induced Breakdown Spectroscopy (LIBS) system and generating analysis results; and
   e) associating, on the database, the analysis results with the unique identifiers.

36. A method for analyzing organic material comprising the steps of:
   a) receiving a sample of organic material, the sample being associated with a unique identifier and to a location where the sample of organic material was taken;
   b) compacting the organic material sample;
   c) analyzing the compacted organic material sample using a Laser Induced Breakdown Spectroscopy (LIBS) system and generating analysis results; and
   d) associating, on a database, the analysis results with the unique identifier of the sample container.

* * * * *